US009638697B2

(12) United States Patent
Hamakubo et al.

(10) Patent No.: US 9,638,697 B2
(45) Date of Patent: May 2, 2017

(54) MONOCLONAL ANTIBODY SPECIFICALLY RECOGNIZING ASPARAGINE SYNTHETASE

(71) Applicants: THE UNIVERSITY OF TOKYO, Tokyo (JP); INSTITUTE OF IMMUNOLOGY CO., LTD., Tokyo (JP); AICHI MEDICAL UNIVERSITY, Aichi (JP)

(72) Inventors: Takao Hamakubo, Tokyo (JP); Yasuhiro Mochizuki, Tokyo (JP); Hiroko Iwanari, Tokyo (JP); Osamu Arai, Tokyo (JP); Toshiyuki Kitoh, Aichi (JP); Masahito Tsurusawa, Aichi (JP)

(73) Assignees: THE UNIVERSITY OF TOKYO, Tokyo (JP); INSTITUTE OF IMMUNOLOGY CO., LTD., Tokyo (JP); AICHI MEDICAL UNIVERSITY, Aichi (JP)

( * ) Notice: Subject to any disclaimer, the term of this patent is extended or adjusted under 35 U.S.C. 154(b) by 0 days.

(21) Appl. No.: 14/348,803

(22) PCT Filed: Oct. 3, 2012

(86) PCT No.: PCT/JP2012/075642
§ 371 (c)(1),
(2) Date: Mar. 31, 2014

(87) PCT Pub. No.: WO2013/051606
PCT Pub. Date: Apr. 11, 2013

(65) Prior Publication Data
US 2014/0322726 A1    Oct. 30, 2014

(30) Foreign Application Priority Data

Oct. 3, 2011 (JP) ................................. 2011-218966

(51) Int. Cl.
*G01N 33/573* (2006.01)
*G01N 33/574* (2006.01)
*C07K 16/40* (2006.01)

(52) U.S. Cl.
CPC ....... *G01N 33/57496* (2013.01); *C07K 16/40* (2013.01); *G01N 33/573* (2013.01); *G01N 33/574* (2013.01)

(58) Field of Classification Search
None
See application file for complete search history.

(56) References Cited

U.S. PATENT DOCUMENTS 6,713,278 B1    3/2004 Bouvier et al.
7,078,189 B2    7/2006 Bouvier et al.

7,439,030 B2    10/2008 Bouvier et al.
7,985,548 B2 *   7/2011 Lorenzi et al. .............. 435/6.11
2009/0311233 A1 *  12/2009 Lorenzi ................. C12N 15/111
424/94.6

FOREIGN PATENT DOCUMENTS

JP    2001-333773        12/2001
JP    2003-052370        2/2003
WO    98/46777           10/1998
WO    WO 2008/013530 A1 * 1/2008 ........... G01N 33/573

OTHER PUBLICATIONS

Asparagine synthetase isoform b (NCBI Reference Sequence: NP_001171546.1 May 13, 2010).*
Van Heeke and Schuster (J. Biol. Chem. 1989 264 (33): 19475-19477).*
Larsen and Schuster (Archives Biochem. Biophys. 1992 299(1): 15-22).*
Hongo et al. (Archives Biochem. Biophys. 1992 295(1): 120-125).*
Richards et al., "Asparagine Synthetase Chemotherapy", *Annu. Rev. Biochem.*, vol. 75, pp. 629-654, 2006.
Kiriyama et al., "Biochemical Characterization of U937 Cells resistant to L-asparaginase: The Role of Asparagine Synthetase", *Leukemia*, vol. 3, No. 4, pp. 294-297, 1989.
Aghaiypour et al., "Structural Basis for the Activity and Substrate Specificity of Erwinia chrysanthemi L-Asparaginase", *Biochemistry*, vol. 40, pp. 5655-5664, 2001.
Ueno et al., "Cell cycle arrest and apoptosis of leukemia cells induced by L-asparaginase", *Leukemia*, vol. 11, pp. 1858-1861, 1997.
Aslanian et al., "Asparagine synthetase expression alone is sufficient to induce L-asparaginase resistance in MOLT-4 human leukaemia cells" *Biochem. J.*, vol. 357, pp. 321-328, 2001.
Scherf et al., "A gene expression database for the molecular pharmacology of cancer", *Nature Genetics*, vol. 24, pp. 236-244, 2000.
Lorenzi et al., "Asaparagine synthetase is a predictive biomarker of l-asparaginase activity in ovarian cancer cell lines", *Mol. Cancer Ther.*, vol. 7, pp. 3123-3128, 2008.
Hutson et al., "Amino acid control of asparagine synthetase: relation to asparginase resistance in human leukemia cells", *Am. J. Physiol.*, vol. 272, pp. C1691-C1699, 1997.
Leslie et al., "Expression levels of asparagine synthetase in blasts from children and adults with acute lymphoblastic leukaemia", *Br. J. Haematol.*, vol. 132, pp. 740-742, 2006.
Stams et al., "Upregulation of asparagine synthetase and cell cycle arrest in t(12;21)-positive ALL", *Leukemia*, vol. 19, pp. 318-319, 2005.
Dübbers et al., "Asparagine synthetase activity in paediatric acute leukaemias: AML-M5 subtype shows lowest activity", *Br. J. Haematol.*, vol. 109, pp. 427-429, 2000.
Abbatiello et al., "Mass spectrometric quantification of asparagine synthetase in circulating leukemia cells from acute lymphoblastic leukemia patients", *J. Proteomics*, vol. 71, pp. 61-70, 2008.

(Continued)

*Primary Examiner* — Peter J Reddig
(74) *Attorney, Agent, or Firm* — Greenblum & Bernstein, P.L.C.

(57) ABSTRACT

It is an object of the present invention to provide a monoclonal antibody, which is suitable for the quantitative analysis of asparagine synthetase in a cell. The present invention provides a monoclonal antibody which specifically recognizes asparagine synthetase that is present in a cell.

7 Claims, 10 Drawing Sheets

(56) References Cited

OTHER PUBLICATIONS

Su et al., "Correlation between Asparaginase Sensitivity and Asparagine Synthetase Protein Content, but not mRNA, in Acute Lymphoblastic Leukemia Cell Lines", *Pediatr. Blood Cancer*, vol. 50, pp. 274-279, 2008.
Lindley et al., "Production of monoclonal antibodies using recombinant baculovirus displaying gp64-fusion proteins", *J. Immunol. Methods*, vol. 234, pp. 123-135, 2000.
Tanaka et al., "The Generation of Monoclonal Antibodies against Human Peroxisome Proliferator-activated Receptors (PPARs)", *J. Atheroscler. Thromb.*, vol. 9, No. 5, pp. 233-242, 2002.
Saitoh et al., "Viral envelope protein gp64 transgenic mouse facilitates the generation of monoclonal antibodies against exogenous membrane proteins displayed on baculovirus", *J. Immunol. Methods*, vol. 322, pp. 104-117, 2007.
Mizushima et al., "pEF-BOS, a powerful mammalian expression vector", *Nucleic Acids Res.*, vol. 18, No. 17, p. 5322, 1990.
Irino et al., "Establishment of Real-Time Polymerase Chain Reaction Method for Quantitative Analysis of Asparagine Synthetase Expression", *J. Mol. Diagnostics*, vol. 6, No. 3, pp. 217-224, 2004.
Stams et al., "Asparagine synthetase expression is linked with l-asparaginase resistance in TEL-AML1-negative but not TEL-AML1-positive pediatric acute lymphoblastic leukemia" *Blood*, vol. 105, pp. 4223-4225, 2005.
Stams et al., "Sensitivity to L-asparaginase is not associated with expression levels of asparagine synthetase in t(12;21)+ pediatric ALL" *Blood*, vol. 101, No. 7, pp. 2743-2747, 2003.
Iwamoto et al., "Mesenchymal cells regulate the response of acute lymphoblastic leukemia cells to asparaginase", *J. Clin. Invest.*, vol. 117, No. 4, pp. 1049-1057, 2007.
Williams, "A New Mechanism of Leukemia Drug Resistance?", *N. Engl. J. Med.*, vol. 357, pp. 77-78, 2007.
Loisel et al., "Recovery of homogeneous and functional $\beta_2$-adrenergic receptors from extracellular baculovirus particles", *Nat. Biotechnol.*, vol. 15, No. 12, pp. 1300-1304, 1997.
Galfre et al., "Preparation of Monoclonal Antibodies: Strategies and Procedures", *Methods in Enzymology*, vol. 73, pp. 3-46, 1981.
Yamada et al., "Clinical relevance of in vitro chemoresistance in childhood acute myeloid leukemia", *Leukemia*, vol. 15, No. 12, pp. 1892-1897, 2001.
Okada et al., "In vitro efficacy of L-asparaginase in childhood acute myeloid leukaemia", *Br. J. Haematol.*, vol. 123, No. 5, pp. 802-809, 2003.
Kitoh et al, "Asparagine Synthetase Protein Expression in Leukemia Cells: Application of L-Asparaginase Treatment for Leukemia", *Blood*, vol. 92, Suppl. 1, pp. 400a, Abstract # 1652, 1998.
Sheng et al., "High-Level Expression of Human Asparagine Synthetase and Production of Monoclonal Antibodies for Enyzme Purification", *Protein Expr. Purif.*, vol. 3, No. 4, pp. 337-346, 1992.
Hatta et al., "Establishment of Flow cytometrical detection of Asparagine Synthetase (AS) protein in leukemia cells", *Cytometry Research*, vol. 15, No. 1, pp. 35-40, 2005.
Kitoh, "Possible Role of L-Asparaginase Treatment for Hematologic and Neoplastic Disease", *Japanese Journal of Pediatric Hematology*, vol. 17, pp. 449-460, 2003.
Shi et al., "Preparation of anti-ASNS monoclonal antibody and detection of ASNS expression in tumor", *Xi Bao Yu Fen Zi Mian Yi Xue Za Zhi (Chin. J. Cell. Mol. Immunol.)*, vol. 27, No. 1, pp. 74-77, 2011.
He et al., "Asparagine synthetase is partially localized to the plasma membrane and upregulated by L-asparaginase in U937 cells", *J. Huazhong Univ. Sci. Technol. Med. Sci.*, vol. 31, No. 2, pp. 159-163, 2011.
Lorenzi et al., "Asparagine synthetase as a causal, predictive biomarker for L-asparaginase activity in ovarian cancer cells" *Mol. Cancer Ther.*, vol. 5, No. 11, pp. 2613-2623, 2006.
Martin et al., "An investigation into the mechanism of L-asparaginase resistance in L5178Y murine leukemia cells", *Amino Acids*, vol. 5, No. 1, pp. 51-69, 1993.
International Preliminary Report on Patentability for PCT/JP2012/075642 mailed May 22, 2014, along with an English language translation.
International Search Report for PCT/JP2012/075642, mailed on Dec. 4, 2012, along with an English language translation.
Office Action issued in Chinese Patent Application No. 201280049699.X, dated Jul. 9, 2015, along with an English language translation.
Kusano-Arai et al., "Evaluation of the Asparagine Synthetase Level in Leukemia Cells by Monoclonal Antibodies", *Hybridoma*, vol. 31, No. 5, pp. 325-332, 2012.
Pfeiffer et al., "Topographical Separation of the Catalytic Sites of Asparagine Synthetase Explored with Monoclonal Antibodies", *Journal of Biological Chemistry*, vol. 262, No. 24, pp. 11565-11570, 1987.
Mehlhaff et al., "Bovine Pancreatic Asparagine Synthetase Explored with Substrate Analogs and Specific Monoclonal Antibodies", *Archives of Biochemistry and Biophysics*, vol. 284, No. 1, pp. 143-150, 1991.
Pfeiffer et al., "Monoclonal Antibodies Specific for Bovine Pancreatic Asparagine Synthetase (Production and Use in Structural Studies)", *Journal of Biological Chemistry*, vol. 261, No. 4, pp. 1914-1919, 1986.
Van Heeke et al., "The N-terminal Cysteine of Human Asparagine Synthetase Is Essential for Glutamine-dependent Activity", *Journal of Biological Chemistry*, vol. 264, No. 33, pp. 19475-19477, 1989.
Iwamoto et al., "Mesenchymal Cells Determine the Response of Acute Lymphoblastic Leukemia Cells to L-Asparaginase", *Blood (ASH Annual Meeting Abstracts)*, vol. 108, No. 11, Part 1, Abstract 833, p. 250A, 2006.
Extended European Search Report for EP Application No. 12838050.8, dated Mar. 5, 2015.
Chinese Office Action issued in CN Patent Application No. 201280049699.X, dated Mar. 29, 2016, along with an English language translation.
Japanese Office Action issued in JP Patent Application No. 2013-537532, mailed Sep. 6, 2016, along with an English language translation.
Chinese Office Action issued in CN Patent Application No. 201280049699.X, dated Oct. 8, 2016, along with an English-language translation.
Eurasian Office Action issued in Eurasian Patent Application No. 201490734 dated Feb. 2, 2017, along with English-language translation.
Office Action issued in Japanese Counterpart Patent Application No. 2013-537532, dated Mar. 21, 2017, along with a machine English translation thereof.

\* cited by examiner

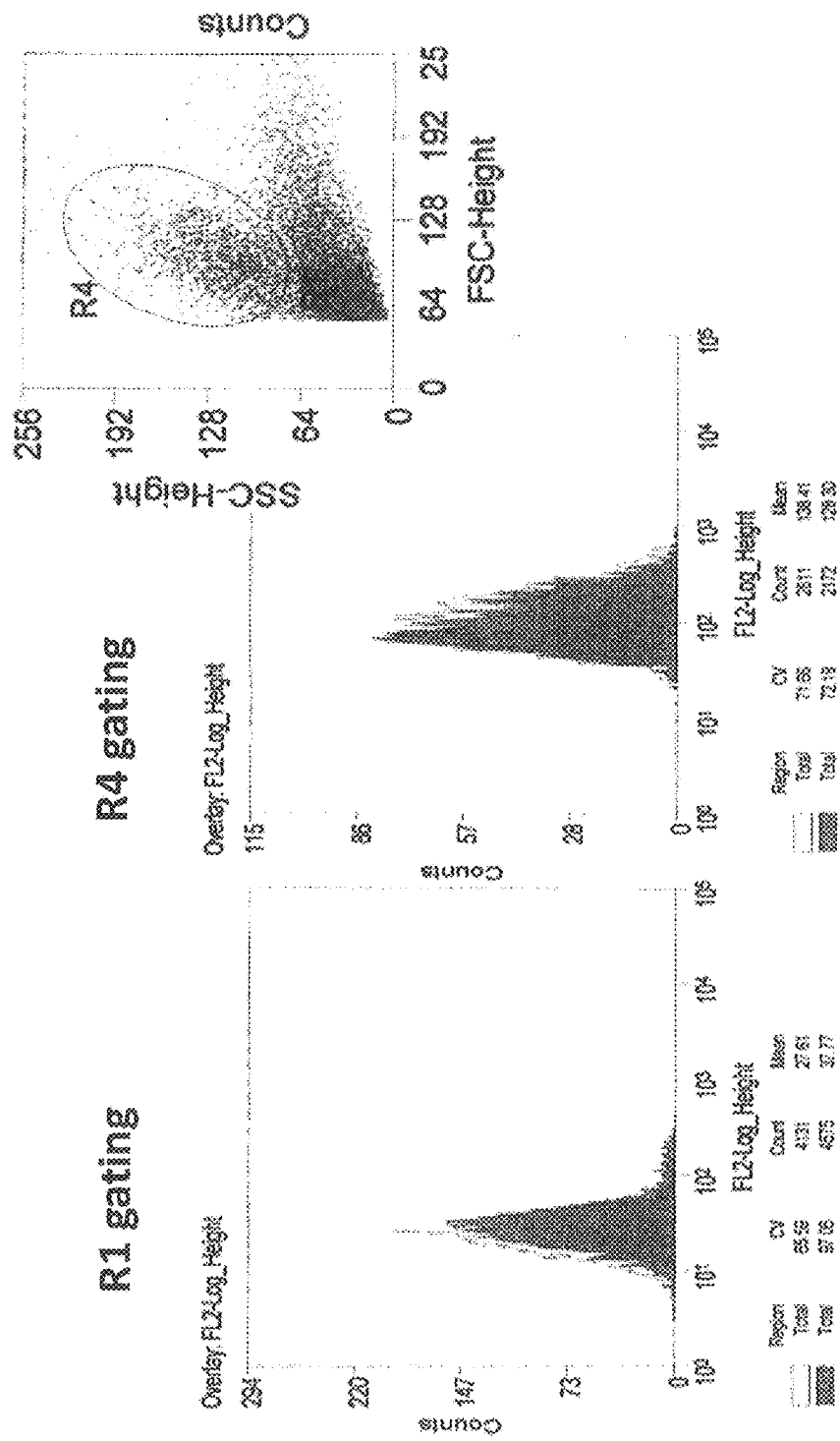
Figure 6 Analysis of peripheral blood sample by Gating

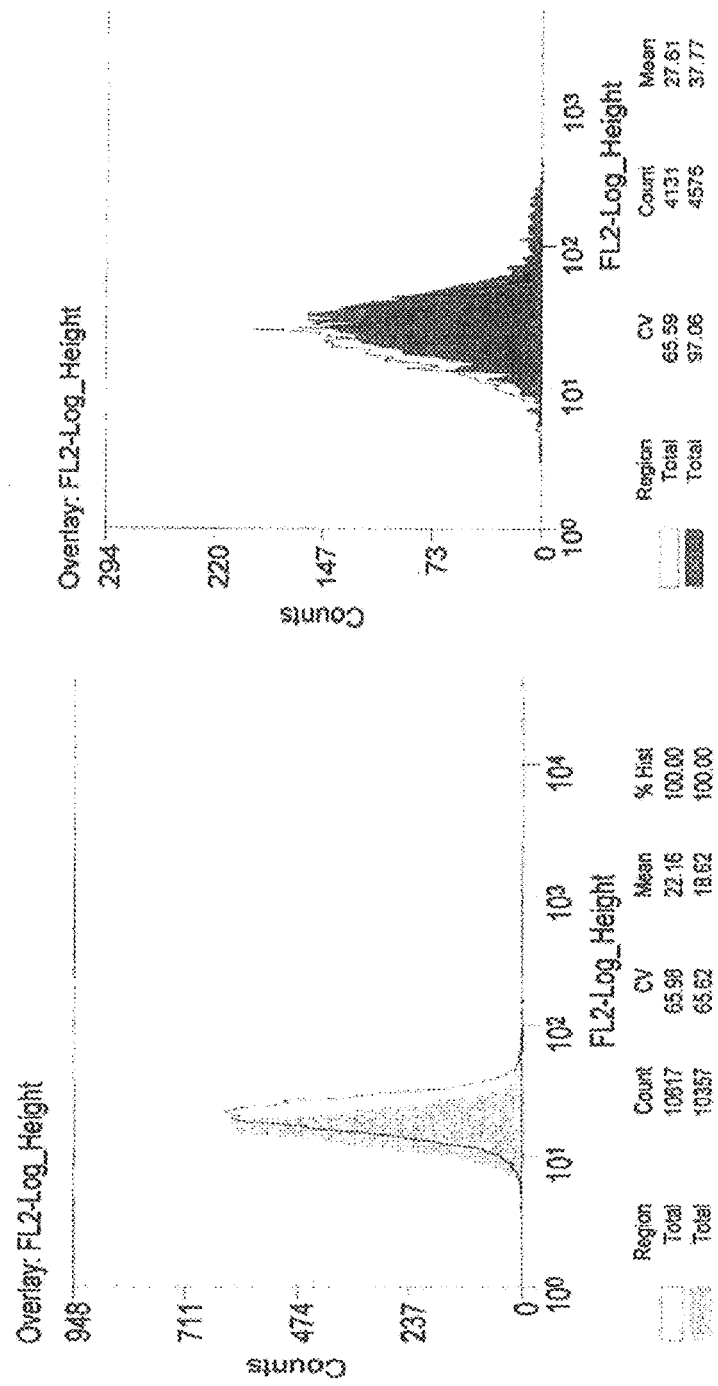

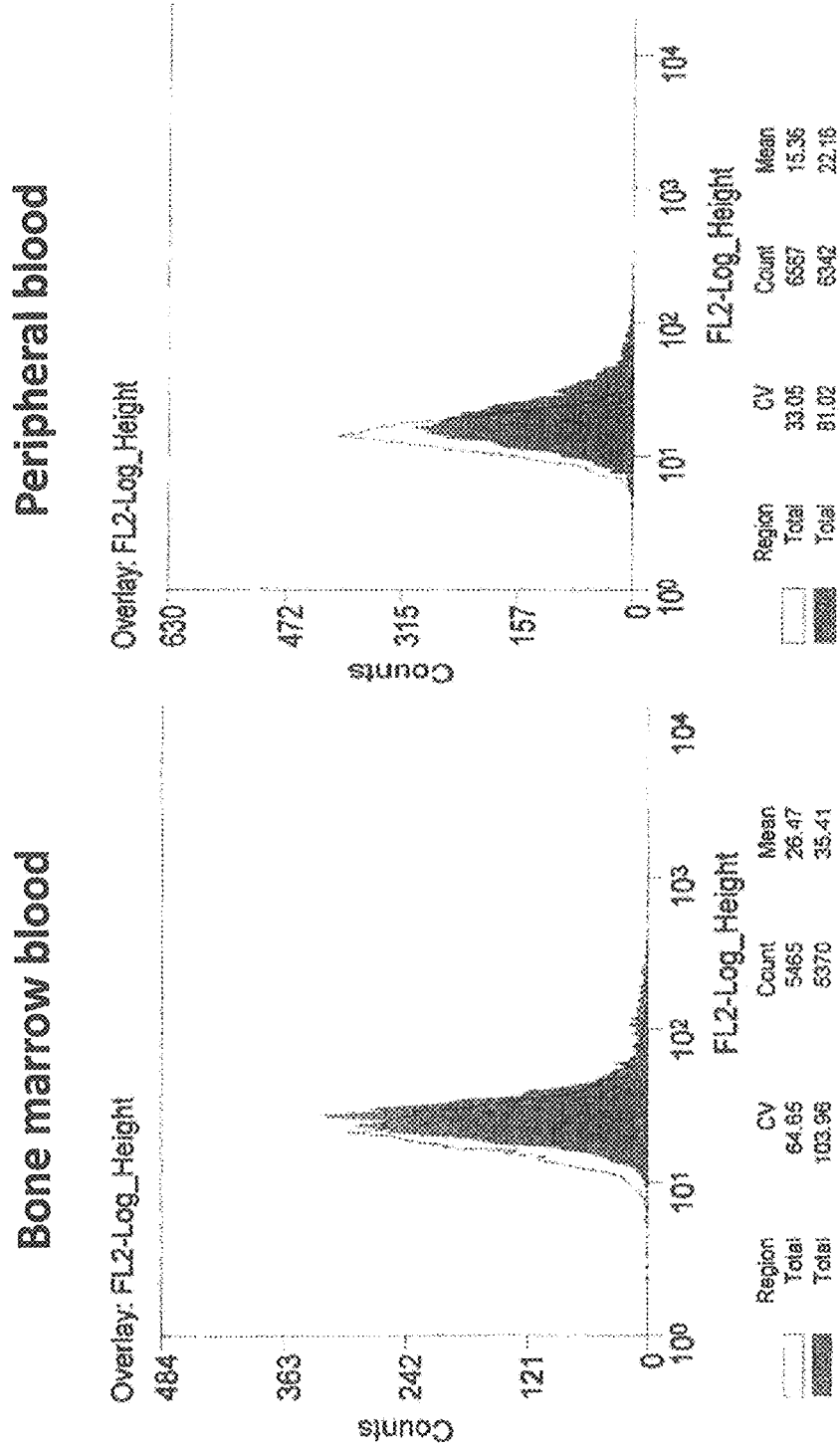
Figure 8. ALL 1y3m Male example: comparison between bone marrow blood and peripheral blood

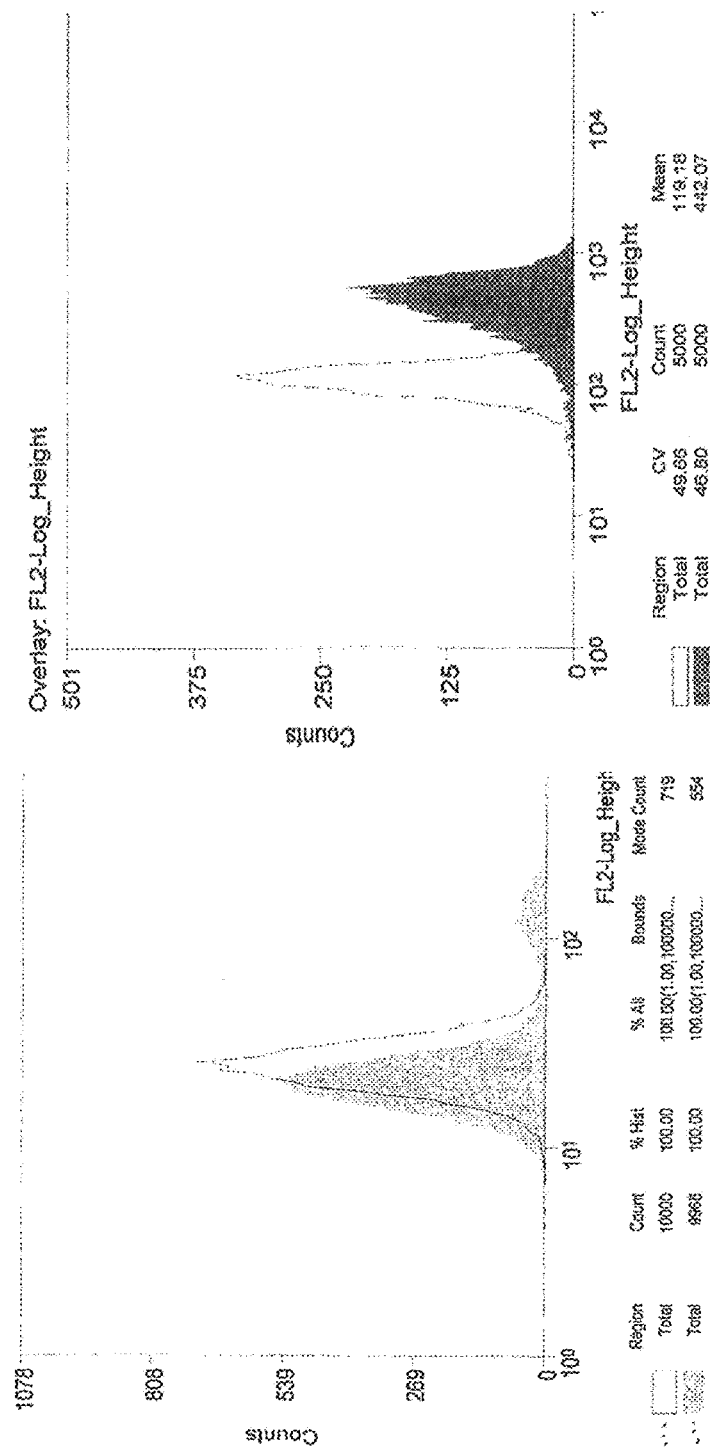
Figure 9. AML case case 4; M1 case 5; M2 MTT assay was performed

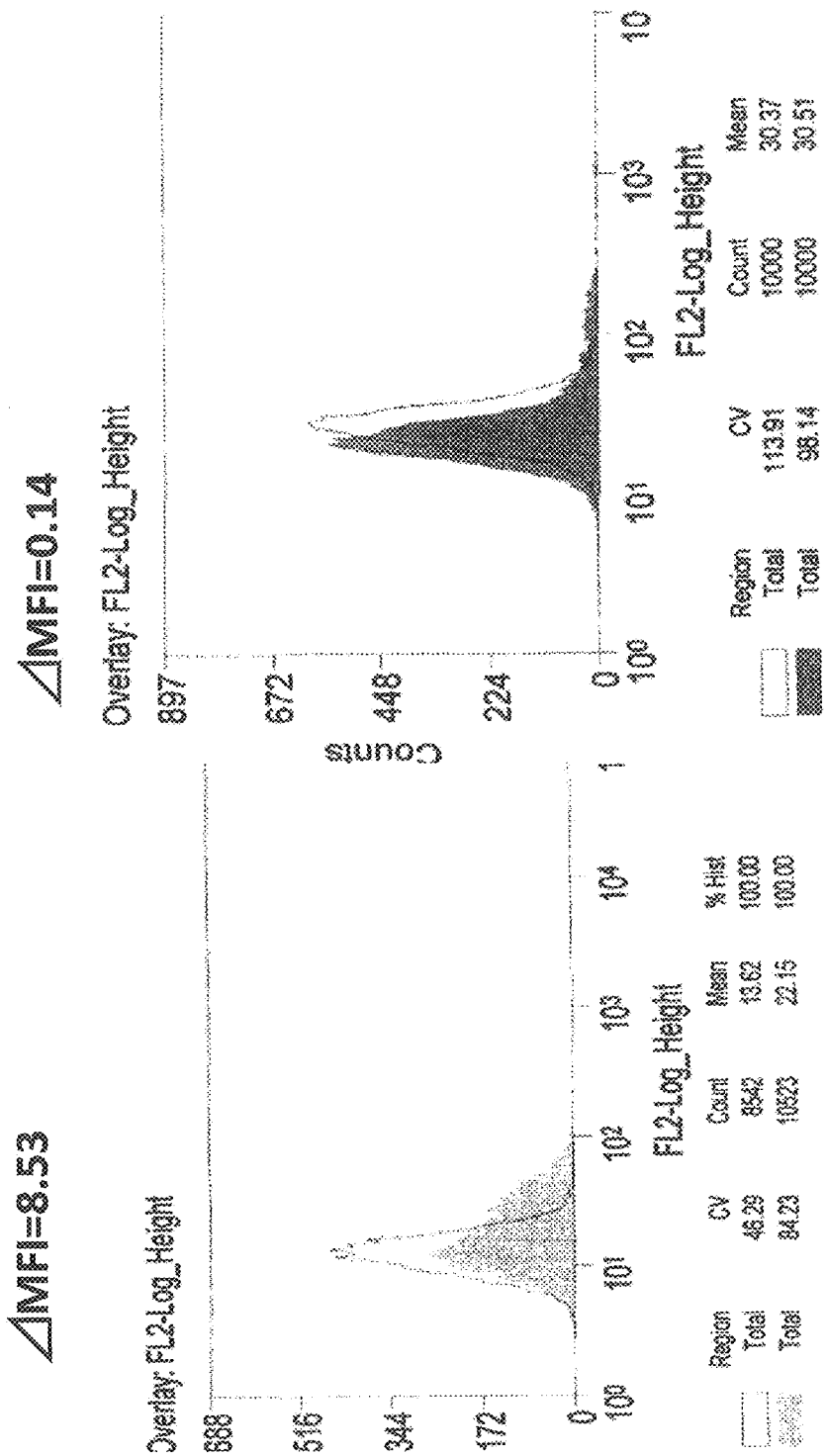

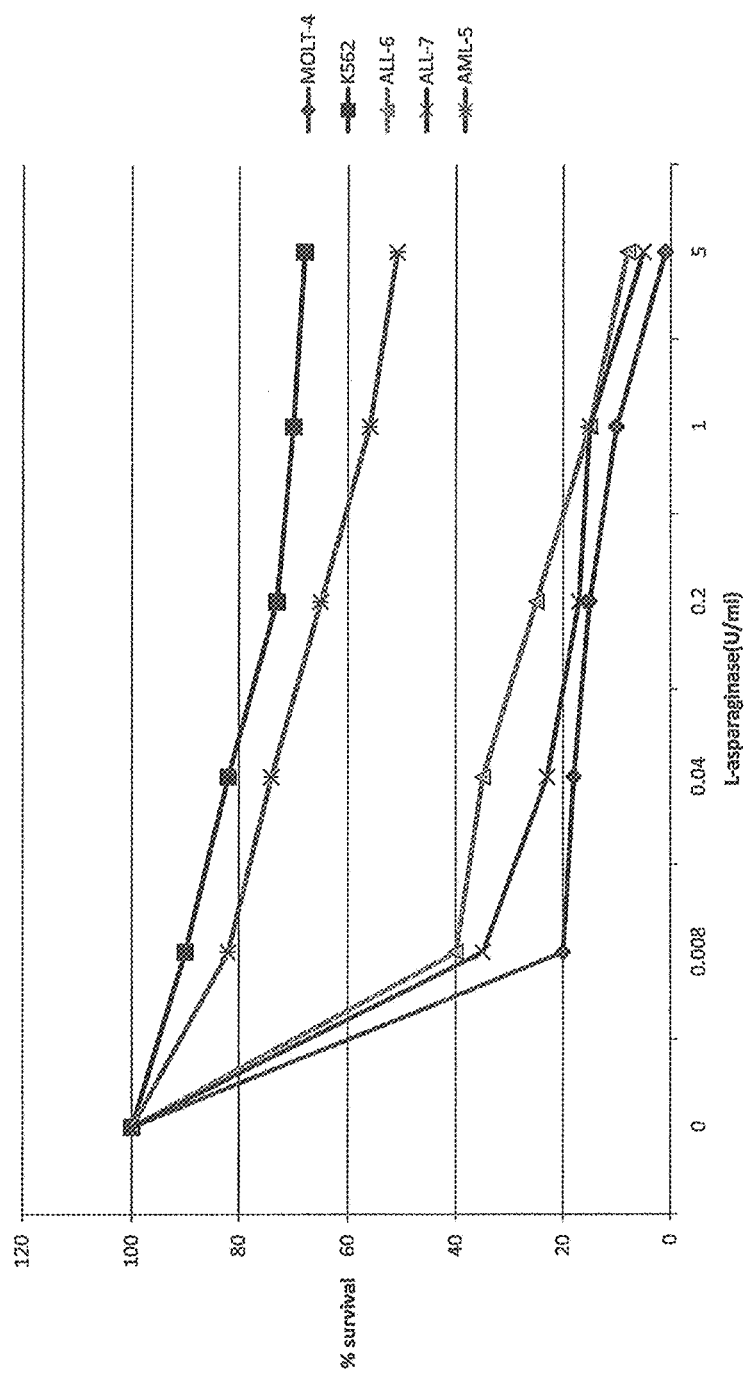
Figure 11. 3 cases, MTT assay of cell lines

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
aactgcagtg tggcatttgg gcgctgttt                                29

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ccgccaaccg gtgaaatcca                                          20

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gaagatctat gtgtggcatt tgggcgctg                                29

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
gaagatctct aagctttgac agctgacttg                               30

MONOCLONAL ANTIBODY SPECIFICALLY RECOGNIZING ASPARAGINE SYNTHETASE

TECHNICAL FIELD

The present invention relates to a monoclonal antibody specifically recognizing asparagine synthetase, and a reagent for measuring asparagine synthetase and a method for measuring asparagine synthetase, both of which use the aforementioned antibody.

BACKGROUND ART

Asparagine synthetase (ASNS) catalyzes the biosynthesis of L-asparagine from L-aspartate in an ATP-dependent reaction for which L-glutamine is used as a nitrogen source in vivo [Non Patent Literature 1]. Accordingly, L-asparagine is not an essential amino acid that must be obtained from outside of the body. If the supply of L-asparagine is decreased in normal cells, it can be compensated by the synthesis of L-asparagine. However, in the case of lymphoblasts, since the activity of ASNS is not sufficient therein, L-asparagine must be obtained from outside [Non Patent Literature 2]. L-asparaginase (ASNase) is an enzyme that hydrolyzes L-asparagine into L-aspartate and ammonia [Non Patent Literature 3], and it is an important drug for the treatment of many cases of acute lymphatic leukemia (ALL). Administration of ASNase causes depletion of L-asparagine in blood, spinal fluid and bone marrow, and it also causes depletion of L-asparagine in cells. Lymphoblast cells with an extremely low ASNS level are susceptible to cell death. In an in-vivo system, the exposure of lymphoblast cells to ASNase terminated the G1 phase and caused apoptosis [Non Patent Literature 4]. It has been demonstrated that overexpression of human ASNS is sufficient for inducing ASNase resistance [Non Patent Literature 5]. The relationship between the expression level of ASNS and sensitivity to ASNase has been observed not only in leukemia cells, but also in ovarian cancer cells [Non Patent Literatures 6 and 7]. These findings suggest the importance of the monitoring of ASNS activity as a diagnostic marker for determining treatment with ASNase. Although the relationship between ASNase resistance and the expression level of ASNS mRNA has been widely reported [Non Patent Literature 8], there have been a few number of studies in which the amount of ASNS protein in human leukemia has been determined [Non Patent Literatures 9-13]. Such a few numbers of reports include a report stating the importance of ASNS protein measurement for the estimation of sensitivity to ASNase [Non Patent Literature 13].

A baculovirus expression system using the insect cell line Sf9 as a host has been used for large scale production of protein. In particular, many researchers including ourselves have demonstrated that a fusion protein with a membrane protein or a virus gp64 protein can be displayed not only on a Sf9 cell, but also on a budded baculovirus (BV) particle. Accordingly, an exogenous protein displayed on BV can be used for immunization, without purification of an antigenic protein [Non Patent Literatures 14, 15, and 16].

PRIOR ART LITERATURES

Non Patent Literature

Non Patent Literature 1: N. G. Richards, M. S. Kilberg, Asparagine synthetase chemotherapy. Annu Rev. Biochem. 75 (2006) 629-54.

Non Patent Literature 2: Y. Kiriyama, M. Kubota, T. Takimoto, T. Kitoh, A. Tanizawa, Y. Akiyama, H. Mikawa, Biochemical characterization of U937 cells resistant to L-asparaginase: the role of asparagine synthetase. Leukemia 3 (1989) 294-7.

Non Patent Literature 3: K. Aghaiypour, A. Wlodawer, J. Lubkowski, Structural basis for the activity and substrate specificity of Erwinia chrysanthemi L-asparaginase. Biochemistry 40 (2001) 5655-64.

Non Patent Literature 4: T. Ueno, K. Ohtawa, K. Mitsui, Y. Kodera, M. Hiroto, A. Matsushima, Y. Inada, H. Nishimura, Cell cycle arrest and apoptosis of leukemia cells induced by L-asparaginase. Leukemia 11 (1997) 1858-61.

Non Patent Literature 5: A. M. Aslanian, B. S. Fletcher, M. S. Kilberg, Asparagine synthetase expression alone is sufficient to induce 1-asparaginase resistance in MOLT-4 human leukaemia cells. Biochem. J. 357 (2001) 321-8.

Non Patent Literature 6: U. Scherf, D. T. Ross, M. Waltham, L. H. Smith, J. K. Lee, L. Tanabe, K. W. Kohn, W. C. Reinhold, T. G Myers, D. T. Andrews, D. A. Scudiero, M. B. Eisen, E. A. Sausville, Y Pommier, D. Botstein, P. O. Brown, J. N. Weinstein, A gene expression database for the molecular pharmacology of cancer. Nat. Genet. 24 (2000) 236-44.

Non Patent Literature 7: P. L. Lorenzi, J. Llamas, M. Gunsior, L. Ozbun, W. C. Reinhold, S. Varma, H. Ji, H. Kim, A. A. Hutchinson, E. C. Kohn, P. K. Goldsmith, M. J. Birrer, J. N. Weinstein, Asparagine synthetase is a predictive biomarker of L-asparaginase activity in ovarian cancer cell lines. Mol. Cancer. Ther. 7 (2008) 3123-8.

Non Patent Literature 8: R. G Hutson, T. Kitoh, D. A. Moraga Amador, S. Cosic, S. M. Schuster, M. S. Kilberg, Amino acid control of asparagine synthetase: relation to asparaginase resistance in human leukemia cells. Am. J. Physiol. 272 (1997) C1691-9

Non Patent Literature 9: M. Leslie, M. C. Case, A. G. Hall, S. A. Coulthard, Expression levels of asparagine synthetase in blasts from children and adults with acute lymphoblastic leukemia. Br. J. Haematol. 132 (2006) 740-2.

Non Patent Literature 10: W. A. Stams, M. L. den Boer, H. B. Beverloo, E. R. van Wering, R. Pieters, Upregulation of asparagine synthetase and cell cycle arrest in t(12;21)-positive ALL. Leukemia 19 (2005) 318-9.

Non Patent Literature 11: A. Dübbers, G. Würthwein, H. J. Müller, P. Schulze-Westhoff, M. Winkelhorst, E. Kurzknabe, C. Lanvers, R. Pieters, G J. Kaspers, U. Creutzig, J. Ritter, J. Boos, Asparagine synthetase activity in paediatric acute leukaemias: AML-M5 subtype shows lowest activity. Br. J. Haematol. 109 (2000) 427-9.

Non Patent Literature 12: S. E. Abbatiello, Y. X. Pan, M. Zhou, A. S. Wayne, T. D. Veenstra, S. P. Hunger, M. S. Kilberg, J. R. Eyler, N. G. Richards, T. P. Conrads, Mass spectrometric quantification of asparagine synthetase in circulating leukemia cells from acute lymphoblastic leukemia patients. J. Proteomics 71 (2008) 61-70.

Non Patent Literature 13: N. Su, Y. X. Pan, M. Zhou, R. C. Harvey, S. P. Hunger, M. S. Kilberg, Correlation between asparaginase sensitivity and asparagine synthetase protein content, but not mRNA, in acute lymphoblastic leukemia cell lines. Pediatr. Blood Cancer 50 (2008) 274-9.

Non Patent Literature 14: K. M. Lindley, J. L. Su, P. K. Hodges, G. B. Wisely, R. K. Bledsoe, J. P. Condreay, D. A. Winegar, J. T. Hutchins, T. A. Kost, Production of monoclonal antibodies using recombinant baculovirus displaying gp64-fusion proteins. J. Immunol. Methods 234 (2000) 123-35.

Non Patent Literature 15: T. Tanaka, T. Takeno, Y. Watanabe, Y. Uchiyama, T. Murakami, H. Yamashita, A. Suzuki, R. Aoi, H. Iwanari, S. Y. Jiang, M. Naito, K. Tachibana, T. Doi, A. I. Shulman, D. J. Mangelsdorf, R. Reiter, J. Auwerx, T. Hamakubo, T. Kodama, The generation of monoclonal antibodies against human peroxisome proliferator-activated receptors (PPARs). J. Atheroscler. Thromb. 9 (2002) 233-42.

Non Patent Literature 16: R. Saitoh, T. Ohtomo, Y Yamada, N. Kamada, J. Nezu, N. Kimura, S. Funahashi, K. Furugaki, T. Yoshino, Y. Kawase, A. Kato, O. Ueda, K. Jishage, M. Suzuki, R. Fukuda, M. Arai, H. Iwanari, K. Takahashi, T. Sakihama, I. Ohizumi, T. Kodama, M. Tsuchiya, T. Hamakubo, Viral envelope protein gp64 transgenic mouse facilitates the generation of monoclonal antibodies against exogenous membrane proteins displayed on baculovirus. J. Immunol. Methods 322 (2007) 104-17.

Non Patent Literature 17: S. Mizushima, S. Nagata, pEF-BOS, a powerful mammalian expression vector. Nucleic Acids Res. 18 (1990) 5322.

Non Patent Literature 18: T. Irino, T. Kitoh, K. Koami, T. Kashima, K. Mukai, E. Takeuchi, T. Hongo, T. Nakahata, S. M. Schuster, M. Osaka, Establishment of real-time polymerase chain reaction method for quantitative analysis of asparagine synthetase expression. J. Mol. Diagn. 6 (2004) 217-24.

Non Patent Literature 19: W. A. Stams, M. L. den Boer, A. Holleman, I. M. Appel, H. B. Beverloo, van E. R. Wering, G. E. Janka-Schaub, W. E. Evans, R. Pieters, Asparagine synthetase expression is linked with L-asparaginase resistance in TEL-AML1-negative but not TEL-AML1-positive pediatric acute lymphoblastic leukemia. Blood 105 (2005) 4223-5.

Non Patent Literature 20: W. A. Stams, den M. L. Boer, H. B. Beverloo, J. P. Meijerink, R. L. Stigter, E. R. van Wering, G. E. Janka-Schaub, R. Slater, R. Pieters, Sensitivity to L-asparaginase is not associated with expression levels of asparagine synthetase in t(12;21)+ pediatric ALL. Blood 101 (2003) 2743-7.

Non Patent Literature 21: S. Iwamoto, K. Mihara, J. R. Downing, C. H. Pui, D. Campana, Mesenchymal cells regulate the response of acute lymphoblastic leukemia cells to asparaginase. J. Clin. Invest. 117 (2007) 1049-57.

Non Patent Literature 22: D. A. Williams, A new mechanism of leukemia drug resistance? N. Engl. J. Med. 357 (2007) 77-8.

SUMMARY OF INVENTION

Problem to be Solved by the Invention

As described above, L-asparaginase (ASNase) is important for the treatment of infantile acute lymphocytic leukemia (ALL). It has been reported that sensitivity to ASNase is related to the protein amount of asparagine synthetase (ASNS) contained in the ALL cell line. However, since a monoclonal antibody suitable for quantitative analysis has not yet been found, there have been only a few reports regarding the amount of an ASNS protein. It is an object of the present invention to provide a monoclonal antibody, which is suitable for the quantitative analysis of asparagine synthetase in a cell.

Means for Solving the Problem

As a result of intensive studies directed towards achieving the aforementioned object, the present inventors have succeeded in producing a monoclonal antibody specifically recognizing asparagine synthetase, which can be applied to flow cytometry or enzyme-linked immunosorbent assay (ELISA). According to this monoclonal antibody, it becomes possible to quantify the amount of an ASNS protein in a leukemia cell and to predict ASNase resistance. The present invention has been completed based on these findings.

Thus, the present invention provides the following invention.

(1) A monoclonal antibody which specifically recognizes asparagine synthetase that is present in a cell.
(2) The monoclonal antibody according to (1), which recognizes the amino acid sequence at the N-terminus of asparagine synthetase.
(3) A monoclonal antibody which is produced by a hybridoma having Accession No. NITE BP-1141 or Accession No. NITE BP-1142.
(4) A hybridoma having Accession No. NITE BP-1141 or Accession No. NITE BP-1142.
(5) A reagent for measuring asparagine synthetase present in a cell, which comprises the monoclonal antibody according to any one of (1) to (3).
(6) A method for measuring asparagine synthetase present in a cell, which comprises a step of allowing the monoclonal antibody according to any one of (1) to (3) to come into contact with a cell containing asparagine synthetase.
(7) The method according to (6), which measures asparagine synthetase present in a leukemia cell or an ovarian cancer cell.
(8) A method for evaluating the sensitivity of leukemia or ovarian cancer to L-asparaginase, which comprises measuring asparagine synthetase by the method according to (6) or (7) and then evaluating the sensitivity of leukemia or ovarian cancer to L-asparaginase based on the measurement results.

Advantageous Effects of Invention

In the present invention, we have succeeded in producing a monoclonal antibody specifically recognizing asparagine synthetase that is present in a cell, using a baculovirus display system. The monoclonal antibody of the present invention can recognize human asparagine synthetase in Western blotting, immunofluorescent staining, flow cytometry, and enzyme-linked immunosorbent assay (ELISA). Using the monoclonal antibody of the present invention, it is possible to quantify the amount of an asparagine synthetase protein in a leukemia cell and to clinically evaluate the sensitivity of leukemia to ASNase.

BRIEF DESCRIPTION OF DRAWINGS

FIG. 6 shows the results of the flow cytometry of Case 1 at a blast percentage of 34.5%.

FIG. 7 shows the results of the flow cytometry of Case 1 (blast percentage: 34.5%) and Case 2 (blast percentage: 24.5%).

FIG. 8 shows the results of the flow cytometry of Case 3 (bone marrow fluid and peripheral blood).

FIG. 9 shows the results of the flow cytometry of Case 4 (AML case).

FIG. 10 shows the results of the flow cytometry of Case 6 and Case 7 (ALL cases).

FIG. 11 shows the results of the MTT assay of the cell lines of 3 cases (Case 5, Case 6, and Case 7).

EMBODIMENTS FOR CARRYING OUT THE INVENTION

Figure 1:
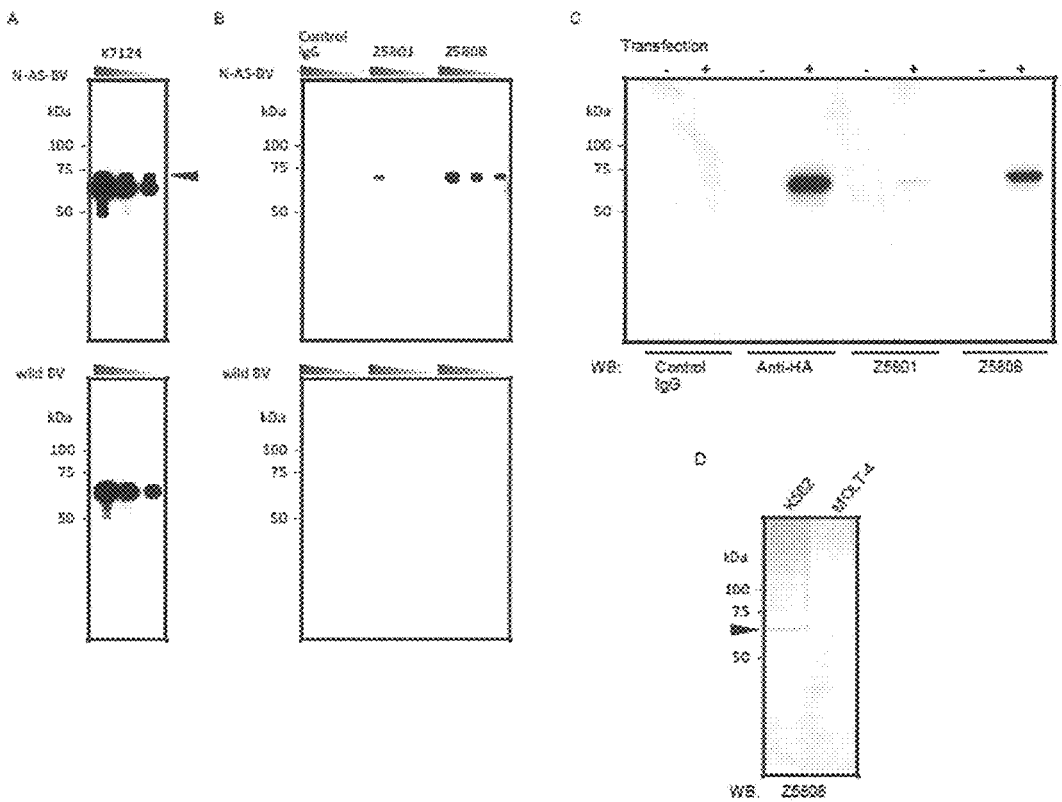
FIG. 1 shows Western blotting in which the produced monoclonal antibody was used. (A) Confirmation of the expression of an N-AS fusion protein. The anti-gp64 monoclonal antibody K7124 was used at a concentration of 1, 0.3, or 0.1 µg/ml. The arrow indicates the band of the N-AS fusion gp64. The upper panel indicates N-AS-BV, and the lower panel indicates wild-type BV. (B) Reactivity with the N-AS fusion protein. Control mouse IgG and anti-ASNS monoclonal antibodies Z5801 and Z5808 were used at a concentration of 1, 0.3, or 0.1 µg/ml. The upper panel indicates N-AS-BV, and the lower panel indicates wild-type BV. (C) Reactivity with HA-ASNS-overexpressing COS7 cell lysate. Protein in a lysate of 10⁴ cells per lane was separated by SDS-PAGE. (+): Lane on which a HA-ASNS-transfected cell lysate was loaded, and (−): Lane on which a non-transfected cell lysate was loaded. As primary antibodies, control mouse IgG, an anti-HA monoclonal antibody (Sigma), and anti-ASNS monoclonal antibodies Z5801 and Z5808 were used at a concentration of 1 μg/ml. (D) Reactivity with endogenous ASNS. Protein in a lysate of $10^5$ cells per lane was separated by SDS-PAGE. As a primary antibody, the antibody Z5808 was used at a concentration of 1 μg/ml. The arrow indicates the band of endogenous ASNS.

Hereinafter, the present invention will be described more in detail.

The antibody of the present invention is a monoclonal antibody specifically recognizing asparagine synthetase that is present in a cell, and is preferably a monoclonal antibody recognizing the amino acid sequence at the N-terminus of asparagine synthetase. In the Examples of the present invention, a general immunization method applied as a common method was not used as a method of obtaining an antibody. Instead, a method of immunizing gp64-expressing transgenic mice with an antigen in which an N-terminal fragment of ASNS was displayed on budded baculovirus (BV antigen) was adopted. That is to say, a preferred example of a method of obtaining the monoclonal antibody of the present invention may be a method of obtaining the monoclonal antibody of the present invention, which comprises recovering N-terminal ASNS displaying budded baculovirus from a culture supernatant of host cells that has been infected with recombinant baculovirus comprising the cDNA of the N-terminal fragment of ASNS, and then immunizing an animal to be immunized with the recovered N-terminal ASNS displaying budded baculovirus used as an antigen. The animal to be immunized is preferably a transgenic mouse that overexpresses gp64.

As described above, in the present invention, budded baculovirus that displays ASNS or a fragment thereof, which is recovered from a culture supernatant of host cells infected with recombinant baculovirus comprising the cDNA of the ASNS or the fragment thereof (e.g. an N-terminal fragment, etc.), is used as an antigen. A method of preparing the budded baculovirus used as an antigen is known. Such budded baculovirus can be prepared according to the methods described, for example, in JP Patent Publication (Kokai) No. 2001-333773 A, JP Patent Publication (Kokai) No. 2003-52370 A, Loisel T P, Ansanay H, St-Onge S, Gay B, Boulanger P, Strosberg A D, Marullo S, Bouvier M., Nat Biotechnol. 1997 November; 15(12): 1300-4., Recovery of homogeneous and functional beta 2-adrenergic receptors from extracellular baculovirus particles; and International Publication WO98/46777.

Specifically, at least one type of recombinant baculovirus comprising the cDNA of ASNS or a fragment thereof (e.g. an N-terminal fragment, etc.) is used. Baculovirus, which transmits to insects and develops disease therein, is an envelope virus having cyclic double-stranded DNA as a gene. This virus shows sensitivity to insects belonging to *Lepidoptera, Hymenoptera, Diptera*, etc. Examples of the baculovirus used as a vector in the present invention include viruses such as *Autographa californica* NPV (AcNPV) of a gamma moth subfamily of NPV and *Bombyx mori* NPV (BmNPV) of a silk worm. An example of host cells (infected and subcultured cells) of AcNPV is *Spodoptera frugiperda* cells (Sf cells). An example of host cells (infected and subcultured cells) of BmNPV is BmN4 cells. The Sf cells have a growth rate higher than that of the BmN4 cells. In addition, AcNPV has an ability to also transmit to human liver cells and human embryonic kidney cells. Thus, an AcNPV vector is preferable. As a host, *Spodoptera Frugiperda* cell lines Sf9 and Sf21 have been established from the ovarian tissues of *S. frugiperda* larva. The cell lines are available from several manufacturers such as Invitrogen or Pharmingen (San Diego, Calif.), or are also available from ATCC. Otherwise, it is also possible to use a living insect larva as a host cell line.

A recombinant virus used in the present invention may be constructed according to a common method. A recombinant virus can be constructed by the following procedures, for example. First, a gene of protein to be expressed is inserted into a transfer vector, so as to construct a recombinant transfer vector. The total size of a transfer vector is generally between approximately several kb to 10 kb. Approximately 3 kb out of the size is a skeleton derived from a plasmid, and it comprises an antibiotic resistance gene that is resistance to antibiotics such as ampicillin and an initiation signal in bacteria DNA replication. A common transfer vector comprises the 5'- and 3'-regions of a polyhedron gene (several kb for each), as well as the aforementioned skeleton. A homologous recombination occurs in these sequences between a gene of interest and the polyhedron gene, when transfection as described below is carried out. Moreover, such a transfer vector preferably comprises a promoter for expression of a protein gene. Examples of such a promoter include a polyhedron gene promoter, a p10 gene promoter, and a capsid gene promoter. The type of such a transfer vector is not particularly limited. Specific examples of such a transfer vector include: AcNPV transfer vectors such as pEVmXIV2, pAcSG1, pVL1392/1393, pAcMP2/3, pAcJP1, pAcUW21, pAcDZ1, pBlueBacIII, pAcUW51, pAcAB3, pAc360, pBlueBacHis, pVT-Bac33, pAcUW1, or pAcUW42/43; and BmNPV transfer vectors such as pBK283, pBK5, pBB30, pBE1, pBE2, pBK3, bPK52, pKBblue, pBKblue2, or pBF series (which are available from Funakoshi Corporation, etc.).

Subsequently, in order to produce a recombinant virus, the aforementioned recombinant transfer vector is mixed with a virus, and the mixture is then introduced into a cultured cell used as a host. Otherwise, the aforementioned transfer vector is introduced into a cultured cell used as a host, which has previously been infected with a virus. Thus, a homologous recombination is allowed to occur between the recombinant transfer vector and the virus genomic DNA, so as to construct a recombinant virus. Examples of the cultured cell used as a host herein include the aforementioned hosts. In general, the cultured insect cells (Sf9 cells, BmN cells, etc.) can be used. Culture conditions are selected by a person skilled in the art, as appropriate. Specifically, when Sf9 cells are used, it is preferable to carry out the culture around 28° C. in a medium that contains 10% fetal bovine serum. The thus constructed recombinant virus can be purified by a common method such as plaque assay. In the thus produced recombinant virus, foreign DNA is substituted with or inserted into the gene region of the polyhedron protein of a nuclear polyhedrosis virus, and thus a polyhedron cannot be formed. Accordingly, such a recombinant virus is easily distinguishable from a non-recombinant virus.

In the method of the present invention, the aforementioned suitable host (the cultured cells of *Spodoptera frugiperda* cell lines Sf9 and Sf21, insect larva, etc.) is infected with the aforementioned recombinant baculovirus. After a certain period of time has passed (72 hours later, for example), an extracellular budded virus (BV) can be recovered from the culture supernatant by a separation operation such as centrifugation. Such an extracellular budded baculovirus can be recovered, for example, as follows. First, the culture of the infected cells is centrifuged at 500 to 3,000 g, so as to recover a supernatant containing an extracellular budded baculovirus. Thereafter, the supernatant is centrifuged at approximately 30,000 to 50,000 g, so as to obtain a precipitate that contains the extracellular budded baculovirus.

The type of the antibody of the present invention is not particularly limited. For example, a mouse antibody, a rat antibody, a rabbit antibody, a sheep antibody, a camel antibody, a chimeric antibody, a humanized antibody, a human antibody or the like can be used, as appropriate. The antibody is a monoclonal antibody. Such a monoclonal antibody can be produced by a method well known to a person skilled in the art. A hybridoma that produces a monoclonal antibody can be produced as follows, basically using a known technique. That is, a desired antigen or a cell expressing such a desired antigen is used as a sensitizing antigen, and it is subjected to immunization according to an ordinary immunization method. The obtained immunocyte is fused with a known parent cell according to an ordinary cell fusion method, and a monoclonal antibody-producing cell (hybridoma) is then screened according to an ordinary screening method, so as to obtain a desired hybridoma. The animal to be immunized can be a mammal such as a mouse, a rat, a rabbit, sheep or a monkey.

A hybridoma can be produced, for example, according to the method of Milstein et al. (Galfre et al., Preparation of Monoclonal Antibodies: Strategies and Procedures, Methods in Enzymology (1981) 73: 3-46).

Regarding the screening for a hybridoma, a hybridoma cell, which produces an ASNS-recognizing antibody, can be selected using a method well known in the present technical field, such as ELISA assay, Western blotting analysis, radioimmunoassay, or FACS using ASNS-expressing cells. A hybridoma secreting a desired antibody is cloned, and the cloned hybridomas are then cultured under suitable conditions. The secreted antibody is recovered, and can be then purified by a method well known in the present technical field, such as ion exchange chromatography, affinity chromatography, etc.

DNA encoding the monoclonal antibody can be easily isolated according to a commonly used method (for example, using an oligonucleotide probe capable of specifically binding to genes encoding the heavy chain and light chain of the monoclonal antibody), and can be then sequenced.

An antibody gene is cloned from hybridomas, and is then incorporated into a suitable vector. The resulting vector is introduced into a host, and a genetically recombinant antibody can be produced by genetic recombination technology and can be then used. Specifically, the cDNA of the variable region (V region) of an antibody is synthesized from the mRNA of the hybridoma, using reverse transcriptase. If DNA encoding the V region of the antibody of interest is obtained, it is ligated to DNA encoding the constant region (C region) of a desired antibody, and the thus ligated DNA is then incorporated into an expression vector. Alternatively, DNA encoding the V region of an antibody may be incorporated into an expression vector comprising the DNA of the antibody C region. The DNA is incorporated into an expression vector, such that it can be expressed under the control of an expression control region such as an enhancer or a promoter. Subsequently, host cells are transformed with this expression vector, so that an antibody can be expressed therein.

As described above, when an antibody is produced by once isolating an antibody gene and then introducing the isolated gene into a suitable host, a combination of a suitable host and a suitable expression vector can be used. When a eukaryote is used as a host, an animal cell, a plant cell, or a fungal cell can be used. Known animal cells used as host cells herein include: (1) mammalian cells, such as CHO, COS, myeloma, BHK (baby hamster kidney), HeLa, or Vero; (2) amphibian cells, such as *xenopus* oocytes; and (3) insect cells, such as sf9, sf21, or Tn5. Known plant cells used as host cells herein include cells derived from genus *Nicotiana* such as *Nicotiana tabacum*. The cells derived from genus *Nicotiana* may be subjected to callus culture. Known fungal cells used as host cells herein include: yeasts including genus *Saccharomyces* such as *Saccharomyces serevisiae*; and filamentous fungi including genus *Aspergillus* such as *Aspergillus niger*. When a prokaryote is used, there is a production system using bacterial cells. Known bacterial cells used herein include *E. coli* and *Bacillus subtilis*. An antibody gene of interest is introduced into these cells by transformation, and the transformed cells are cultured in vitro, so as to obtain an antibody.

These antibodies may also be low-molecular-weight antibodies such as antibody fragments, modified antibodies, or the like, so long as it does not lose the property of recognizing ASNS protein. Specific examples of an antibody fragment include Fab, Fab', F(ab')2, Fv, and Diabody. In order to obtain such an antibody fragment, a gene encoding the antibody fragment may be constructed, it may be then introduced into an expression vector, and it may be then expressed in suitable host cells, using the expression vector. As a modified antibody, an antibody that binds to various types of molecules such as polyethylene glycol (PEG) can be used.

The antibody, which was expressed and produced as described above, can be purified by a known method used for ordinary protein purification. The antibody can be separated and purified, for example, by selecting an affinity column such as a protein A column, a chromatography column, a filter, ultrafiltration, salting-out, dialysis, and the like, and then combining them, as appropriate.

The antibody of the present invention can be used to measure asparagine synthetase present in a cell. That is to say, according to the present invention, there is provided a method for measuring asparagine synthetase present in a cell, which comprises a step of allowing the antibody of the present invention to come into contact with a cell containing asparagine synthetase. In particular, using the antibody of the present invention, the number of molecules of asparagine synthetase (ASNS) in a single cell can be evaluated. In the present invention, it is possible to measure the amount of asparagine synthetase that is particularly present in leukemia cells such as lymphoblasts or ovarian cancer cells, and to evaluate the sensitivity of leukemia or ovarian cancer to L-asparaginase, based on the obtained measurement results.

The present invention will be more specifically described in the following examples. However, these examples are not intended to limit the scope of the present invention.

EXAMPLES

Example 1

(1) Materials and Method (1-1) Preparation of Antigen (N-Terminal ASNS Displaying BV) and Immunization Method The cDNA in the N-terminal region of ASNS (which consists of 2 to 51 amino acid residues and is hereinafter referred to as "N-AS") was amplified by a PCR method, using Human Fetal Brain Marathon-Ready cDNA (Clontech) as a template, and also using 5'-AACTGCAGTGTG-GCATTTGGGCGCTGTTT-3' (SEQ ID NO: 1) and 5'-CCGCCAACCGGTGAAATCCA-3' (SEQ ID NO: 2) as primers. The amplified cDNA was ligated to a gp64 gene. A recombinant virus, into which the N-AS gene had been introduced, was prepared according to the descriptions of the above-mentioned Non Patent Literatures 15 and 16. Seventy-two hours after the infection, the budded virus (N-AS-BV) was recovered from a Sf9 culture solution by centrifugation at 40,000 g for 40 min, and the thus recovered budded virus was then used as an immunogen. In order to avoid an immune response to gp64, a gp64 transgenic mouse was used for immunization according to the descriptions of Non Patent Literature 16. Specifically, 0.1 µg of pertussis toxin used as an adjuvant was mixed with 70 µg of N-AS-BV, and the obtained mixture was then administered into the abdominal cavity of the gp64 transgenic mouse for immunization. As a booster, 70 µg of N-AS-BV that did not contain an adjuvant was administered to the mouse twice at an interval of 2 weeks. Three days after the final immunization, splenic cells were separated, and they were then fused with mouse myeloma cells NS-1 at a mixing ratio of 1:10 according to a standard method. The fused cells were cultured in a HAT selection medium (0.1 mM hypoxanthine, 0.1 mM aminopterin, and 0.16 mM thymidine) for 7 days. Eight days after the cell fusion, a culture supernatant of hybridomas was recovered, and ELISA and Western blotting were performed on N-AS-BV, so as to select antibody-producing cells. The ELISA using antigen-expressing BV was carried out according to the descriptions of Non Patent Literature 16.

(1-2) Cell Lines and Transfected Cell Lines

K562 cells and MOLT-4 cells were purchased from the Cell Bank of RIKEN BioResource Center. The K562 cells were subjected to a suspension culture in an F-12 Nutrient Mixture (Ham's F-12) medium (Invitrogen) in 7% $CO_2$, at 37° C., whereas the MOLT-4 cells were subjected to a suspension culture in an RPMI 1640 medium in 7% $CO_2$, at 37° C., wherein both mediums contain 10% fetal bovine serum, penicillin and streptomycin. In order to prepare HA-tagged human ASNS, human ASNS cDNA was amplified by a PCR method, using Human Fetal Brain Marathon-Ready cDNA (Clontech) as a template, and also using 5'-GAAGATCTATGTGTGGCATTTGGGCGCTG-3' (SEQ ID NO: 3) and 5'-GAAGATCTCTAAGCTTTGACAGCT-GACTTG-3' (SEQ ID NO: 4) as primers. The amplified cDNA was ligated to a pEF-BOS-HA vector [Non Patent Literature 17]. The expression construct was transfected into COS7 cells (ATCC), using Lipofectamine (registered trademark) 2000 reagent (Invitrogen) in accordance with the manufacturer's instructions.

(1-3) Western Blotting

The cells were recovered and were then dissolved in a RIPA buffer (150 mM NaCl, 1% NP-40, 0.1% SDS, 50 mM Tris-HCl (pH 7.9), and 0.5% sodium deoxycholate). The protein contained in the cell lysate was separated by 12% polyacrylamide gel electrophoresis, and was then transferred on a nitrocellulose membrane (GE healthcare). Non-specific binding to the transfer membrane was blocked with Block-Ace (Dainippon Pharmaceutical Co., Ltd.), and a primary antibody was then allowed to react therewith. The resulting transfer membrane was washed with TBS-T (0.05% Tween 20/10 mM Tris-buffered saline), and it was then allowed to react with a 10,000-fold diluted horseradish peroxidase (HRP)-conjugated goat anti-mouse antibody (Jackson ImmunoResearch Laboratories). Thereafter, a protein was detected using SuperSignal West Dura Extended Duration Substrate (Thermo). For detection of a gp64 fusion protein, the gp64 protein-specific antibody K7124 [Non Patent Literature 16], which we had produced by immunization of wild-type baculovirus, was used. Control IgG (3423, 2AHB12) was purchased from Institute of Immunology, Co., Ltd. (Tokyo, Japan).

(1-4) Immunofluorescent Staining

HA-ASNS-transfected COS7 cells were cultured on a cover glass. Thereafter, the cells were immobilized with 4% paraformaldehyde/phosphate-buffered saline (PBS), and were then subjected to a membrane permeation treatment using 0.1% Triton X-100/PBS. After the cells had been blocked with BlockAce, the cells were allowed to react with a mixed solution of an anti-HA polyclonal antibody and an ASNS monoclonal antibody Z5801 or Z5808 (10 μg/ml each), used as a primary antibody, and the resulting cells were then washed with PBS. Subsequently, the cells were allowed to react with a mixed solution of Alexa (registered trademark) fluor 488-labeled anti-rabbit IgG (Invitrogen) and Alexa (registered trademark) fluor 647-labeled anti-mouse IgG (Invitrogen) (each 200-fold diluted). The resulting cover glass was mounted on a slide glass, using ProLong (registered trademark) Gold antifade reagent with DAPI (Invitrogen). The image was taken using a fluorescence microscope (LEICA DB LB, Leica Microsystems).

(1-5) Flow Cytometry

The immobilization treatment and the membrane permeation treatment of the cells were carried out using IntraStain, Fixation and Permeabilization Kit for Flow Cytometry (Dako) in accordance with the manufacturer's instructions. A primary antibody, together with a membrane permeation treatment reagent, was added to the cells to a concentration of 3 μg/ml. The resulting cells were washed with a dilution buffer (1% BSA/0.1 mM EDTA/PBS), and were then allowed to react with R-Phycoerythrin (R-PE)-labeled anti-mouse IgG (Jackson ImmunoResearch Laboratories) that had been 100 times diluted with a dilution buffer. Finally, the cells were washed with a dilution buffer twice, and were then analyzed with a flow cytometer (GUAVA (registered trademark) EasyCyte™ Plus System, Millipore).

(1-6) Enzyme-Linked Immunosorbent Assay $1 \times 10^7$ cells were subjected to a membrane permeation treatment with 0.1 ml of 0.2% Saponin/protease inhibitor cocktail (Complete (registered trademark), Roche)/saline for 15 min at room temperature. Thereafter, a cell-crushed matter was removed by centrifugation at 20,000×g for 10 min. The obtained supernatant was used as a cell extract.

The monoclonal antibody Z5801 was diluted to a concentration of 4 μg/ml with a saline, and it was then solid-phased on a polystyrene 96-well plate (Greiner). After blocking with BlockAce/saline, the cell extract, which had been 20 to 160 times diluted, as appropriate, with a reaction solution (0.1% Saponin/50% BlockAce/saline), was added to each well, and the obtained mixture was then reacted at room temperature for 2 hours. Subsequently, the plate used in the reaction was washed with a washing solution (0.05% Tween 20/saline) five times. A biotinylated monoclonal antibody Z5808 was diluted to a concentration of 1 μg/ml with the reaction solution, and the thus diluted antibody was used as a detection antibody. Biotinylation was carried out using EZ-Link (registered trademark) Sulfo-NHS-LC-Biotin (Thermo) in accordance with the manufacturer's instructions. Finally, the reaction plate was washed, Streptavidin-PolyHRP40 (Stereospecific Detection Technologies) was then 2000 times diluted with the reaction solution, and the resultant was then added to each well. In an enzymatic reaction, TMB Soluble Reagent (ScyTek Laboratories) was used for detection. The enzymatic reaction was terminated using TMB Stop Buffer (ScyTek Laboratories), and the absorbance at 450 nm was then measured using a microplate reader (Biotrak II, GE Healthcare).

(2) Results (2-1) Production of Anti-ASNS Monoclonal Antibody

The expression of a fusion protein of N-AS and virus gp64 was confirmed by Western blotting using the anti-gp64 monoclonal antibody K7124. This antibody recognized the 64-kDa bands of both of N-AS-BV and wild-type BV (FIG. 1A), and also recognized approximately 70 kDa that was an N-AS fusion gp64 protein (FIG. 1A, upper panel, arrow). In order to produce an anti-ASNS monoclonal antibody, a gp64 transgenic mouse was immunized with the budded virus (N-AS-BV), and thereafter, the splenic cells of the mouse were fused with mouse myeloma cells NS-1. Eight days after the cell fusion, a culture supernatant of the hybridomas was selected by Western blotting performed on BV-ELISA and N-AS-BV. Finally, two positive clones Z5801 and Z5808, which specifically reacted with N-AS-BV in both of ELISA and Western blotting, were obtained (FIG. 1B). The subclasses of these antibodies were identified to be IgG2a and kappa, using Mouse Typer (registered trademark) Sub-Isotyping kit (BIO-RAD).

A hybridoma cell that produces the monoclonal antibody Z5801 (which is referred to as "Z5801" for identification) was deposited with the National Institute of Technology and Evaluation (NITE), Patent Microorganisms Depositary (NPMD) (2-5-8, Kazusa Kamatari, Kisarazu-shi, Chiba-ken, Japan, postal code: 292-0818), under Accession No. NITE P-1141 on Sep. 7, 2011. Thereafter, this strain was transferred to an international deposition under the provisions of the Budapest Treaty on Aug. 23, 2012, and received Accession No. NITE BP-1141.

A hybridoma cell that produces the monoclonal antibody Z5808 (which is referred to as "Z5808" for identification) was deposited with the National Institute of Technology and Evaluation (NITE), Patent Microorganisms Depositary (NPMD) (2-5-8, Kazusa Kamatari, Kisarazu-shi, Chiba-ken, Japan, postal code: 292-0818), under Accession No. NITE P-1142 on Sep. 7, 2011. Thereafter, this strain was transferred to an international deposition under the provisions of the Budapest Treaty on Aug. 23, 2012, and received Accession No. NITE BP-1142.

(2-2) Specificity of Anti-ASNS Antibody

Figure 2:
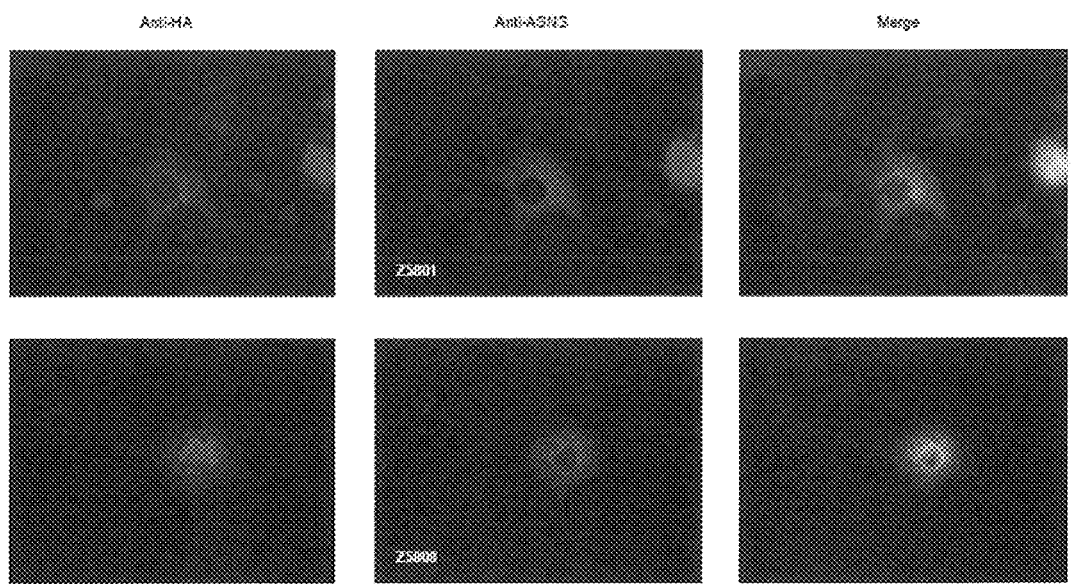
FIG. 2 shows the immunofluorescent staining of HA-ASNS-overexpressing COS7 cells. As a primary antibody, a rabbit anti-HA polyclonal antibody (Sigma) was mixed with a mouse anti-ASNS monoclonal antibody (Z5801 or Z5808) to result in each concentration of 10 μg/ml, and the obtained mixture was then reacted with the cells. The green color indicates the expression of HA-ASNS with the use of the fluorescence of Alexa fluor 488. The red color indicates the reactivity of the anti-ASNS antibody with HA-ASNS with the use of the fluorescence of Alexa fluor 647. The blue color indicates a cell nucleus stained with DAPI.

The reaction specificity of these monoclonal antibodies to full-length ASNS was confirmed using HA-ASNS-overexpressing COS7 cells. In Western blotting using a lysate of the aforementioned cells, these monoclonal antibodies recognized a band with a molecular weight of 64 kDa of the HA-ASNS cDNA-transfected cells, in the same manner as the anti-HA antibody did (FIG. 1C). Moreover, Z5808 also recognized ASNS endogenously present in K562 cells (FIG. 1D). In immunofluorescent staining, these monoclonal antibodies recognized HA-ASNS-expressing cells, in the same manner as the anti-HA antibody did (FIG. 2).

(2-3) Application of Anti-ASNS Antibody to Flow Cytometry

Figure 3:
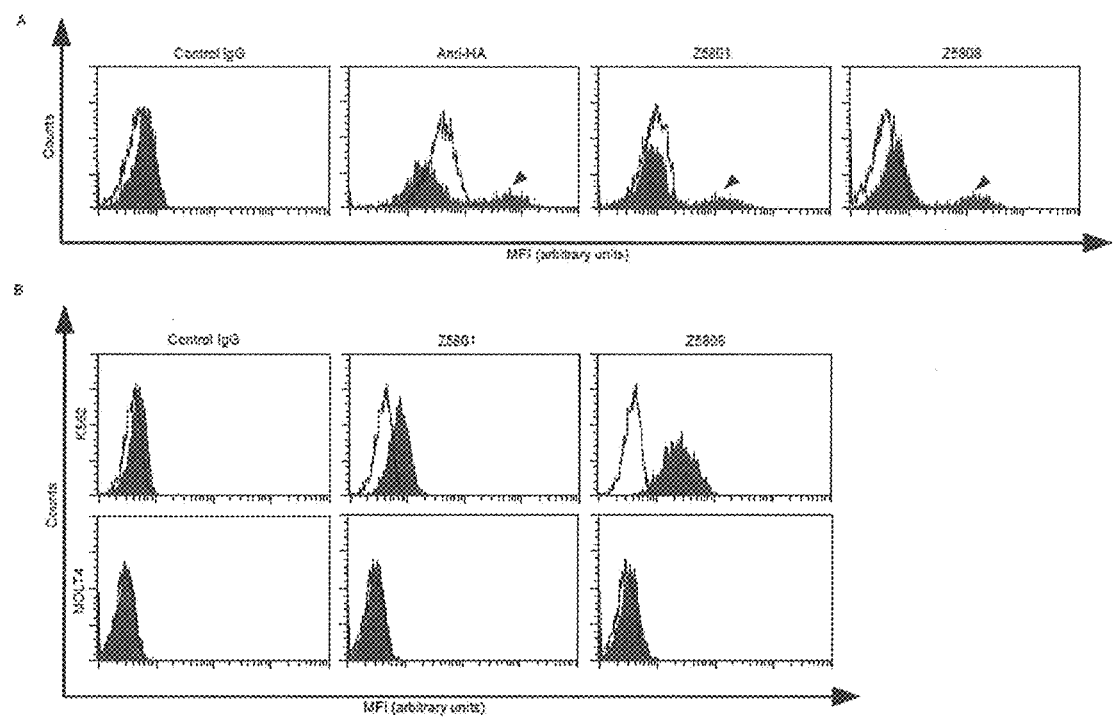
FIG. 3 shows application of an anti-ASNS monoclonal antibody to flow cytometry. (A) The analysis of HA-ASNS-transfected COS7 cells by flow cytometry. The filled histogram shows HA-ASNS-transfected COS7 cells, and the open histogram shows non-transfected COS7 cells. As primary antibodies, control mouse IgG, an anti-HA monoclonal antibody (Sigma), and anti-ASNS monoclonal antibodies Z5801 and Z5808 were used at a concentration of 3 μg/ml. The arrow indicates HA-ASNS-expressing COS7 cells on the shifted histogram. (B) The analysis of endogenous ASNS by flow cytometry. The filled histogram shows the cells with which the primary antibody was allowed to react, and the open histogram shows the cells with which only a secondary antibody was allowed to react. The primary antibody was used at a concentration of 3 μg/ml.

In order to confirm whether or not these anti-ASNS antibodies can be used for flow cytometry, HA-ASNS-overexpressing COS7 cells were subjected to an immobilization treatment and a membrane permeation treatment, using a Dako Intrastain kit. Thereafter, the resulting cells were stained with the anti-HA monoclonal antibody, or with the monoclonal antibody Z5801 or Z5808. As a result, the anti-ASNS monoclonal antibodies Z5801 and Z5808 showed a specific histogram shift, as with the anti-HA antibody (FIG. 3A). Subsequently, whether or not these antibodies recognize endogenous ASNS in flow cytometry was confirmed using the leukemia cell lines K562 and MOLT-4. It had been reported that the expression level of ASNS is high in the cell line K562 and is extremely low in the cell line MOLT4 [Non Patent Literature 17]. As a result, both of the monoclonal antibodies specifically recognized K562 cells and showed a histogram shift (FIG. 3B). In flow cytometry, the reactivity of Z5808 was higher than the reactivity of Z5801.

(2-4) Quantification of the Amount of ASNS Protein by Flow Cytometry

Figure 4:
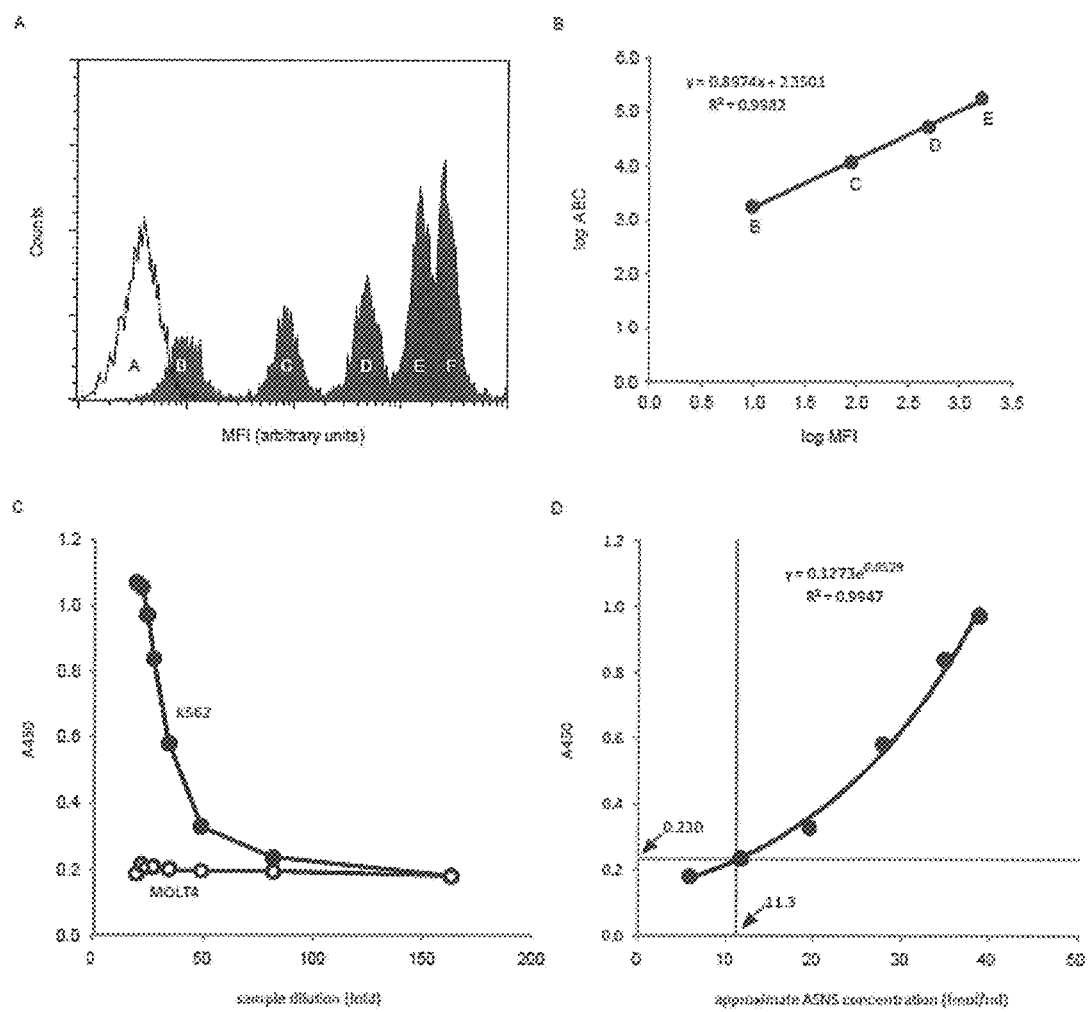
FIG. 4 shows the quantification of ASNS proteins in K562 cells. (A) The histogram of QIFIKIT (registered trademark) calibration beads. Each of six types of beads had the following antibody binding capacity (ABC): A; 0, B; 1,800, C; 12,000, D; 53,000, E; 185,000, and F; 530,000. (B) A calibration curve showing the MFI (Mean Fluorescence Intensity) of four types of calibration beads (B to E) to ABC on a log-log scale. (C) Construction of ASNS measurement sandwich ELISA. The filled circle indicates reactivity with a K562 cell extract, and the open circle indicates reactivity with a dilution series of MOLT-4 cells. Data are shown as mean values from dual measurement. (D) A calibration curve shown with any given ASNS concentration and the absorbance at 450 nm. The detection limit of the ASNS concentration is 11.3 fmol/ml, when A450 is 0.23.
Figure 5:
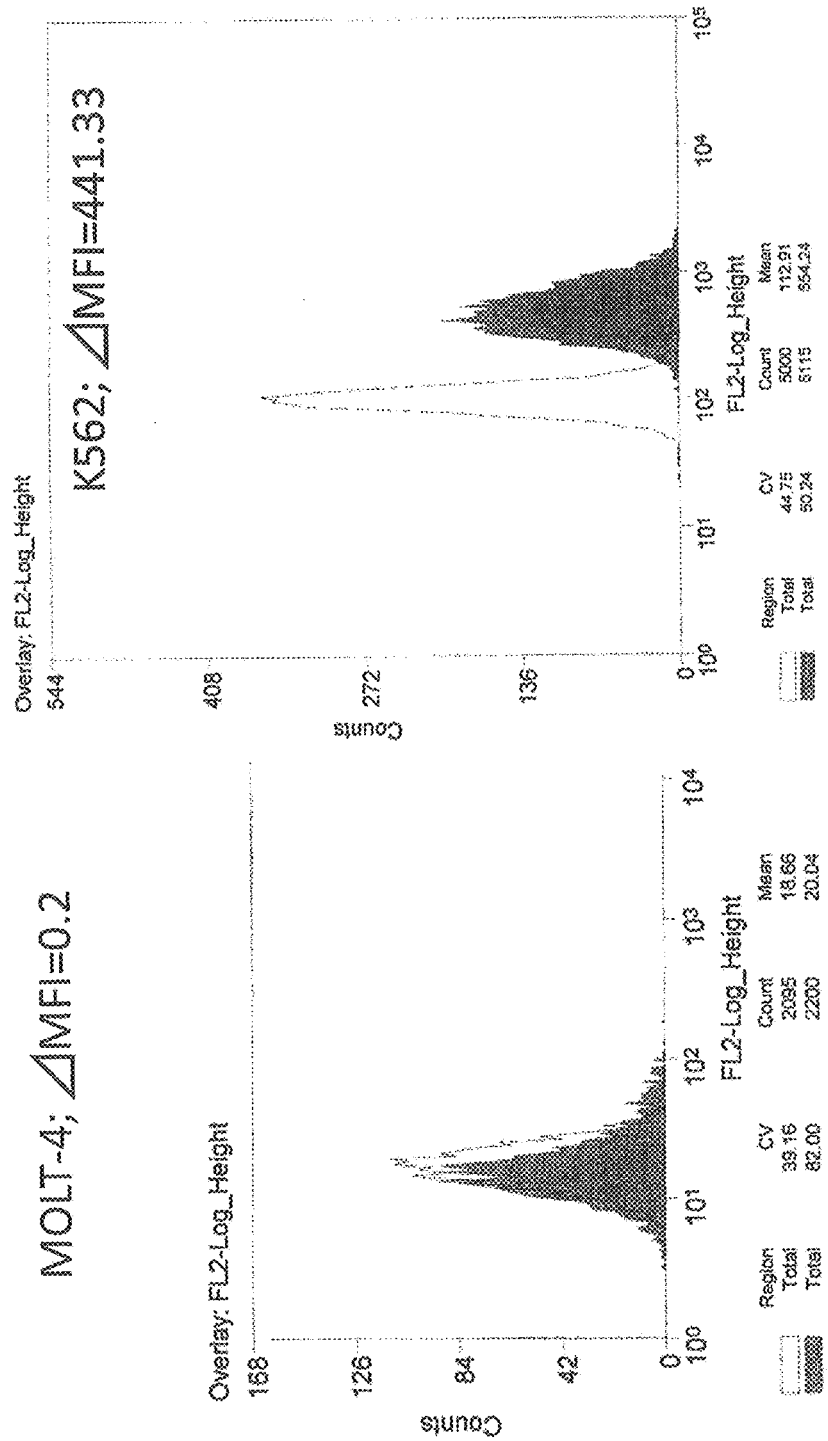
FIG. 5 shows the results of the flow cytometry of MOLT-4 and K562, and Δ MFI difference.

A quantification method using flow cytometry was carried out using QIFIKIT (registered trademark) (Dako) in accordance with the manufacturer's instructions. First, the titer of Z5808 acting as a primary antibody in K562 cells was measured, and the concentration of saturated solution was determined to be 3 μg/ml (data not shown). Using calibration beads of QIFIKIT (registered trademark), the monoclonal antibody binding ability of a cell was obtained based on mean fluorescence intensity (MFI) at the aforementioned concentration. Six types of calibration beads were stained with an R-PE-labeled anti-mouse IgG antibody, as in the case of the cells (FIG. 4A). In this experiment, since the calibration beads F exceeded the measurement limit, the calibration beads B, C, D and E were plotted on a log-log scale (FIG. 4B). A calibration curve was prepared by a least-square method, and using the thus prepared calibration curve, antibody binding capacity (ABC), which indicates antibody binding ability, was obtained based on the MFI value of the sample. In order to quantify the amount of an ASNS protein in K562 cells and MOLT4 cells, the MFI value was estimated at a Z5808 or control IgG concentration of 3 μg/ml, and it was then corrected with control IgG The cells were analyzed using a flow cytometer, and ABC was then calculated according to the formula of the calibration curve (FIG. 4B). If it were assumed that the molecular weight of ASNS in a single cell would be equal to ABC, the following equation could be held:

ASNS molecules per cell=ABC(Z5808)−ABC(control IgG)

The estimated number of ASNS molecules per cell was 5800 in the case of a K562 cell, and was 80 in the case of a MOLT-4 cell (Table 1).

TABLE 1

Number of ASNS molecules expressed in K562 cells and MOLT-4 cells

|  | MFI (arbitrary units) | | ABC (units/cell) | | ASNS (molecules/cell) |
| --- | --- | --- | --- | --- | --- |
|  | Z5808 | Control IgG | Z5808 | Control IgG |  |
| MOLT-4 | 3.60 | 3.17 | 707 | 631 | 76 |
| K562 | 43.62 | 4.56 | 6631 | 874 | 5757 |

(2-5) Construction of ASNS Measurement ELISA

Upon construction of ASNS quantification ELISA, the anti-ASNS monoclonal antibody Z5801 was used as a capture antibody, and biotinylated Z5808 was used as a detection antibody. In order to amplify measurement sensitivity, Streptavidin-PolyHRP40 was used as a detection enzyme. Using this measurement system, ASNS could be detected in a K562 cell extract, but it could not be detected in a MOLT-4 cell extract (FIG. 4C). If the number of ASNS molecules in a K562 cell were estimated to be 5800 molecules/cell by flow cytometry, any given ASNS concentration would be 960 fmol/ml, when the $10^7$ cells are extracted with 1 ml of extraction buffer. The extract was diluted at any given ASNS concentration ranging from 38 fmol/ml to 6 fmol/ml, and a calibration curve was prepared (FIG. 4D). The detection limit of this measurement system was determined to be absorbance 450 nm (A450)=0.23 (mean+3SD), based on a dilution series of MOLT-4 cell extract that was ASNS-negative. The calibration curve was prepared as an exponential function according to a least-square method (FIG. 4D). The detection limit of the ASNS concentration was calculated to be 11.3 fmol/ml.

(3) Consideration

The importance of determining the amount of an ASNS protein in a leukemia cell for prediction of the therapeutic effects of ASNase has been reported [Non Patent Literatures 12 and 13]. The mechanism of ASNase resistance has not yet been elucidated. The phenomena of ASNase resistance are related to some patients with an increased ASNS expression level. However, that is not for all cases, and it depends on each patient [Non Patent Literatures 19 and 20]. In the present example, an anti-ASNS monoclonal antibody, which can be applied not only to flow cytometry and ELISA, but also to Western blotting and immunofluorescent staining, was produced. There have been several reports regarding the use of an anti-ASNS antibody [Non Patent Literatures 7, 8, and 12], but there have been no reports regarding the anti-ASNS monoclonal antibody that can be used in flow cytometry. Flow cytometry for quantification of ASNS would be useful for a clinical diagnosis for predicting the effects of ASNase. In addition, it was also confirmed that sandwich ELISA could be constructed using the two antibodies. Colorimetric ELISA is a simple and easy measurement system, and construction of colorimetric ELISA for quantification of ASNS would also be useful for clinical diagnoses. There are two advantages for using a baculovirus protein display system for production of a monoclonal antibody. The first advantage is that a process of purifying a protein, which is hardly obtained in an amount sufficient for immunization, can be omitted, and that it is very easy to prepare an antigen called an "antigen-displaying baculovirus." The second advantage is that, since baculovirus itself has a strong adjuvant effect, a high-affinity antibody capable of recognizing a natural protein can be obtained. In contrast, a great disadvantage of this technique is the strong immunogenicity of the virus. In order to overcome this disadvantage, a mouse, into which a gp64 gene as a coat protein gene of the viruses had been introduced, was produced. This gp64 gene transgenic mouse has immunologic tolerance to gp64, and it has extremely low reactivity with viruses [Non Patent Literature 16]. According to the monoclonal antibody of the present invention, it becomes possible to elucidate the relationship between the amount of an ASNS protein and ASNase resistance, which can construct a novel measurement system for quantifying the amount of an ASNS protein by flow cytometry or ELISA. There is a novel finding regarding ASNase resistant leukemia. Mesenchymal cells in the bone marrow release a large amount of asparagine and make a defense niche for leukemia cells. Thus, asparagine supplied from other cells protects leukemia cells from a treatment with ASNase and causes them to survive. In several cases of children who had undergone this drug therapy, leukemia recurred. This phenomenon might be caused by leukemia cells, which were resistant to ASNase in the defense niche of the bone marrow and survived. The expression level of ASNS in mesenchymal cells suggests the ASNase resistance of leukemia cells in the bone marrow [Non Patent Literatures 21 and 22]. Hence, in order to predict sensitivity to ASNase, it is important to histologically quantify ASNS in mesenchymal cells. The anti-ASNS monoclonal antibody of the present invention is useful for elucidating the defense mechanism of mesenchymal cells for leukemia cells.

Example 2

(1) Materials and Method

The bone marrow fluid or peripheral blood of patients with leukemia was used. The cell lines MOLT-4 and K562, the ASNS activity of each of which had been known, were used as a negative control and a positive control, respectively, and an MTT assay was carried out. The cell line was cultured in an RPMI1640 medium containing 10% fetal bovine serum, and the cells at the logarithmic growth phase were adjusted to be a cell density of 3 to $10\times10^6$/ml, and were then used. In several cases, the MTT assay was carried out to determine the presence or absence of L-ASNase resistance and sensitivity.

(1-1) Flow Cytometry (FCM)

An immobilization treatment and a membrane permeation treatment were performed on cells using IntraStain, Fixation and Permeabilization Kit for Flow Cytometry (Dako) in accordance with the manufacturer's instructions. The used monoclonal antibody Z5808 is a culture supernatant of hybridomas having Accession No.: NITE BP-1142, and it has a kappa chain and belongs to the IgG2a class. A primary antibody, as well as a membrane permeation treatment reagent, was added to the cells to a concentration of 10 µg/ml. The resulting cells were washed with a dilution buffer (1% BSA/0.1 mM EDTA/PBS), and thereafter, PE-labeled Goat anti-mouse IgG antibody (DAKO) (a secondary antibody) was added to the cells to a concentration of 10 µg/ml, so that they were reacted. Finally, the cells were washed with a dilution buffer twice, and were then analyzed with a flow cytometer (MoFlo (registered trademark) XDP IntelliSort II System, BECKMAN COULTER).

(1-2) Confirmation of Sensitivity to ASNase; MTT Assay

In the case of clinical test samples, mononuclear cells are separated from bone marrow or peripheral blood containing leukemia cells or malignant tumor cells, or from a cell suspension, according to a gradient centrifugation method using Ficoll-Paque (Sigma). After completion of the separation of mononuclear cells, it is confirmed that the cells account for 80% or more of the mononuclear cells, and that the cell survival rate is 95% or more. In the case of MOLT-4 and K562, the cells at the logarithmic growth phase were adjusted to be a cell density of 3 to $10\times10^6$/ml, and were then used. Using a 96-well plate (Falcon), mononuclear cells were cultured in a culture medium that did not contained any drug or contained serially diluted ASNase (RPMI1640 containing 10% fetal bovine serum) in 5% $CO_2$ at 37° C. for 4 days. The final concentration of ASNase was set to be 0.008 to 5.00 U/ml [Yamada, S., et al., Clinical relevance of in vitro chemoresistance in childhood acute myeloid leukemia. Leukemia, 2001. 15(12): p. 1892-7]. The number of mononuclear cells per well (100 µl of culture solution) was set to be $3\times10^5$ in the case of ALL, and $1\times10^5$ in the case of AML. According to 4-day-culture methyl-thiazol-tetrazolium (MTT) assay, the cell-killing rate in an ASNase-added well was calculated, using a no drug-added well as a control. Based on a dose response curve, the concentration of ASNase showing a cell-killing rate of 50% (LD50asp) was obtained [Okada, S., et al., In vitro efficacy of 1-asparaginase in childhood acute myeloid leukaemia. Br J Haematol, 2003. 123(5): p. 802-9].

(1-3) Immunocytochemistry (ICC)

The cells were subjected to a semi-quantitative analysis according to an immunostaining method [Kitoh, T., et al., Asparagine Synthetase Protein Expression in Leukemia Cells: Application of L-Asparaginase Treatment for Leukemia. Blood, 1998. 92(Suppl. 1): p. 400a], using the previously reported another antibody (10 µg/ml), anti-human ASNS antibody (monoclonal antibody 3G hybridoma culture supernatant; mouse IgG2a kappa 30 ug/ml) [Sheng, S., et al., High-level expression of human asparagine synthetase and production of monoclonal antibodies for enzyme purification. Protein Expr Purif, 1992. 3(4): p. 337-46]. Thereafter, it was confirmed that the obtained results were matched with the results of FCM. Specifically, an unstained smear was immobilized with ethanol, and was then blocked with endogenous peroxidase. After that, the smear was incubated with a culture supernatant of 3G6 hybridomas used as a primary antibody at 37° C. for 16 minutes. As a secondary antibody, an avidin-biotin-peroxidase-labeled anti-IgG antibody was used. For staining, DAB Detection Kit (Ventana Medical Systems) was used, and an automatic immunohistochemistry system (EX-IHC, Ventana Medical Systems, Tucson, Ariz.) was employed. Color was developed with 3,3-diaminobenzidine and was then visualized [Irino, T., et al., Establishment of real-time polymerase chain reaction method for quantitative analysis of asparagine synthetase expression. J Mol Diagn, 2004. 6(3): p. 217-24].

(2) Results (2-1)

As previously reported, the measurement of the enzymatic activity of ASNS and estimation of the number of ASNS molecules per cell by the ELISA method had been carried out in the Erythroleukemia-derived cell line K562 (in which ASNS is expressed at a high level) and in the T-ALL-derived cell line MOLT-4 (in which ASNS is expressed at a low level). As shown in Table 1, the ratio is considered to be approximately 90-75:1. In the flow cytometry method using the monoclonal antibody Z5808 (FIG. 1), when the mean fluorescence intensity (MFI) was evaluated based on AMFI obtained by subtracting the mean value of a negative control (M1 MFI) from the total MFI (ALL MFI), the AMFI value was found to be 441.33 in K562, and 0.02 in MOLT-4. Thus, a good correlation was found between the MFI value and each ASNS enzymatic activity. With regard to sensitivity to L-ASNase, it was highly resistant in K562 (>1 U/ml) and highly sensitive in MOLT-4 (<0.1 U/ml).

TABLE 2

|  | ASNS Enzymatic activity | ID50 ASNase (U/ml) | ∆ MFI | ASNS ICC |
|---|---|---|---|---|
| K562 | 558 ± 56.2 | >5 | 441.33 | (+++) |
| MOLT-4 | 18.4 ± 3.5 | <0.1 | 0.02 | (−) |

A summary of studies cases is shown in Table 3 below.

TABLE 3

| Case | Sex | Age | Test sample | blast percentage | FAB Classification | ∆ MFI | ASNS ICC |
|---|---|---|---|---|---|---|---|
| Case 1 | F | 3 yr. | bone marrow fluid | 34.5% | AML M7 | 12.34 | (−) |
| Case 2 | F | 8 days | peripheral blood | 24.5% | TAM M7 | 8.38 | (−) |
| Case 3 | M | 1 yr. 3 mon. | peripheral blood | 20% | ALL L1 | 7.55 | (−) |
| Case 3' | M | 1 yr. 3 mon. | bone marrow fluid | 98% | ALL L1 | 7.65 | (−) |
| Case 4 | M | 79 yr. | peripheral blood | 42% | AML M1 | 11.65 | (±) |
| Case 5 | M | 80 yr. | peripheral blood | 95% | AML M2 | 322.9 | (++) |
| Case 6 | M | 6 yr. | bone marrow fluid | 95% | ALL L1 | 3.54 | (−) |
| Case 7 | F | 14 yr. | bone marrow fluid | 98% | ALL L1 | 0.14 | (−) |

(2-2) Results in the Case of Peripheral Blood

The results of the flow cytometry of Case 1 with a blast percentage of 34.5% are shown in FIG. 6. Blasts were specified by performing gating on a scatter distribution, and the ASNS protein in the cytoplasm could be quantified.

Almost the same results were obtained from Case 2 and Case 3 (FIG. 7 and FIG. 8). In Case 3, when the results of bone marrow blood were compared with the results of peripheral blood, if 20% or more of blasts were contained therein, there could be obtained almost the same results as those of FCM performed on cell lines or bone marrow blood containing 90% or more of blasts.

AML cases: In Case 4 that was M1 in the FAB classification, ASNS was expressed at a low level. In Case 5 that was M2 in the FAB classification, ASNS was expressed at a high level (FIG. 9). In this case, an MTT assay was also carried out.

Also, the ALL2 case, on which the MTT assay was carried out, is shown in FIG. 10. In both cases, ASNS was expressed at a low level.

The results of the MTT assay performed on the cell lines of three cases are shown in FIG. 11. In Case 5 (AML M2) (which is indicated as "AML-5" in FIG. 11), the cells showed resistance equivalent to that of 1(562 cells (highly expressing ASNS and resistant to L-ASNase). In two ALL cases (Case 6 and Case 7; which are indicated as "ALL-6" and "ALL-7" in FIG. 11), the cells showed sensitivity equivalent to that of MOLT-4 that is a T-ALL cell line. A summary of the relationship between ASNS expression and sensitivity to L-ASNase is shown in Table 4. It is apparent that there is a relationship in which as the expression level increases, sensitivity to L-ASNase attenuates. In contrast, it is anticipated that a case with a low expression of ASNS would be more sensitive to L-ASNase.

TABLE 4

|  | ∆ MFI | ID50 ASNase (U/ml) |
|---|---|---|
| K562 | 441.33 | >5.0 |
| AML-5 | 322.9 | 5 |
| ALL-6 | 8.53 | <0.01 |
| ALL-7 | 0.14 | <0.01 |
| MOLT-4 | 0.20 | <0.01 |

(3) Consideration

Flow cytometry (FCM) was carried out using the monoclonal antibody Z5808, and the expression of asparagine synthetase (ASNS) in tumor cells was detected with fluorescence. The ∆ MFI value (=the MFI of Z5808−the MFI of isotype control) in FCM reflected the amount of an ASNS protein, and a majority of ALL cases and AML cases were classified into leukemia associated with a low amount of ASNS protein. Some AML cases were classified into leukemia associated with a high amount of ASNS protein. As a result of the studies regarding sensitivity to L-asparaginase according to the MTT assay, the ID50 of the AML case associated with a high amount of ASNS protein was >5 U/ml, showing L-asparaginase resistance, and the ID50 of the two ALL cases associated with a low amount of ASNS protein was <0.01 U/ml (sensitivity). The measurement of the amount of the ASNS protein by FCM was considered to give useful information for predicting sensitivity to L-asparaginase.

The invention claimed is:

1. A monoclonal antibody which is produced by a hybridoma having Accession No. NITE BP-1141 or Accession No. NITE BP-1142.

2. A hybridoma having Accession No. NITE BP-1141 or Accession No. NITE BP-1142.

3. A reagent for measuring asparagine synthetase present in a cell, which comprises the monoclonal antibody according to claim 1.

4. A method for measuring asparagine synthetase present in a cell, which comprises allowing the monoclonal antibody according to claim 1 to come into contact with a cell containing asparagine synthetase.

5. The method according to claim 4, which measures asparagine synthetase present in a leukemia cell or an ovarian cancer cell.

6. A method for evaluating the sensitivity of leukemia or ovarian cancer to L-asparaginase, which comprises measuring asparagine synthetase by the method according to claim 4 and then evaluating the sensitivity of leukemia or ovarian cancer to L-asparaginase based on the measurement results.

7. A method for evaluating the sensitivity of leukemia or ovarian cancer to L-asparaginase, which comprises measuring asparagine synthetase by the method according to claim 5 and then evaluating the sensitivity of leukemia or ovarian cancer to L-asparaginase based on the measurement results.

* * * * *